US009040268B2

(12) United States Patent
Datta et al.

(10) Patent No.: US 9,040,268 B2
(45) **Date of Patent: *May 26, 2015**

(54) METHOD FOR CONTROLLING UNDESIRABLE BYPRODUCTS FORMATION CAUSED BY CONTAMINATING ORGANISMS IN THE PRODUCTION OF ETHANOL FROM SYNGAS

(75) Inventors: Rathin Datta, Chicago, IL (US); Andrew Reeves, Chicago, IL (US); Laura T. Kliman, Chicago, IL (US)

(73) Assignee: Coskata, Inc., Warrenville, IL (US)

(*) Notice: Subject to any disclaimer, the term of this patent is extended or adjusted under 35 U.S.C. 154(b) by 6 days.

This patent is subject to a terminal disclaimer.

(21) Appl. No.: 13/619,547

(22) Filed: Sep. 14, 2012

(65) Prior Publication Data

US 2013/0071897 A1 Mar. 21, 2013

Related U.S. Application Data

(63) Continuation-in-part of application No. 13/239,305, filed on Sep. 21, 2011, now Pat. No. 8,551,746.

(51) Int. Cl.

| | |
|---|---|
| ***C12P 7/54*** | (2006.01) |
| ***C12P 7/04*** | (2006.01) |
| ***C12P 7/52*** | (2006.01) |
| ***C12P 39/00*** | (2006.01) |
| ***C12P 7/06*** | (2006.01) |
| ***C12P 7/14*** | (2006.01) |

(52) U.S. Cl.

CPC ... *C12P 7/04* (2013.01); *C12P 7/52* (2013.01); *C12P 7/54* (2013.01); *Y02E 50/17* (2013.01); *C12P 39/00* (2013.01); *C12P 7/065* (2013.01); *C12P 7/14* (2013.01)

(58) Field of Classification Search

CPC ................ C12P 7/06; C12P 7/04; C12P 7/52; C12P 7/54

See application file for complete search history.

(56) References Cited

U.S. PATENT DOCUMENTS

| | | | | |
|---|---|---|---|---|
| 8,551,746 B2 * | 10/2013 | Reeves et al. | ................ | 435/140 |
| 2012/0135538 A1 | 5/2012 | Zhao | | |

OTHER PUBLICATIONS

Li, F. et al., Coupled Ferredoxin and Crotonyl Coenzyme A (CoA) Reduction with NADH Catalyzed by the Butyryl-CoA Dehydrogenase/Etf Complex from *Clostridium kluyveri,* Journal of Bacteriology, Feb. 2008, vol. 190, No. 3, p. 843-850.

Vincent Massey, et al., Mechanistic Studies with General Acyl-CoA Dehydrogenase and Butyryl-CoA Dehydrogenase: Evidence for the Transfer of the ,&Hydrogen to the Flavin N(5)-Position as a Hydridet, Biochemistry 1984, 23, pp. 3154-3161.

Robert H. Abeles, et al., Mechanism of Action of Butyryl-CoA Dehydrogenase: Reactions with Acetylenic, Olefinic, and Fluorinated Substrate Analogues, Biochemistry 1982, 21, pp. 6685-6695.

Jung-Ja P. Kim, Three-Dimensional Structure of Butyryl-CoA Dehydrogenase from *Megasphaera elsdenii,* Biochemistry 1995,34, pp. 2163-2171.

* cited by examiner

*Primary Examiner* — Alexander Kim

(57) ABSTRACT

A method of operating a fermentation zone for the production of ethanol from syngas uses a crotonate-like compound to prevent or reverse the effects of butyrogen contamination. The crotonate-like compound works in continuous fermentation processes to reduce or eliminate contamination from butyrate and butanol in the syngas derived ethanol product.

19 Claims, 6 Drawing Sheets

METHOD FOR CONTROLLING UNDESIRABLE BYPRODUCTS FORMATION CAUSED BY CONTAMINATING ORGANISMS IN THE PRODUCTION OF ETHANOL FROM SYNGAS

CROSS REFERENCE TO RELATED APPLICATION

This is a continuation in part of U.S. patent application Ser. No. 13/239,305, filed Sep. 21, 2011, now U.S. Pat. No. 8,551,746 B-2, from which priority is claimed, which application is hereby incorporated by reference in its entirety.

FIELD OF THE INVENTION

This invention pertains to processes for the low energy, anaerobic bioconversion of hydrogen and carbon monoxide in a gaseous substrate stream to oxygenated $C_2$ compounds such as ethanol by contact with microorganisms in a fermentation system with high conversion efficiency of both hydrogen and carbon monoxide. The method of this invention reduces production of undesirable byproducts such as butyric acid, butanol and other longer chain organic acids or alcohols that result from bacterial contaminants in the fermentation system.

BACKGROUND

Bioethanol production for use as a liquid motor fuel is increasing worldwide. Such biofuels include, for example, ethanol that can be blended with gasoline with a wide range of compositions. One of the major drivers for bioethanol is its derivation from renewable resources by fermentation and bioprocess technology. Conventionally, biofuels are made from readily fermentable carbohydrates such as sugars and starches. For example, the two primary agricultural crops that are used for conventional bioethanol production are sugarcane (Brazil and other tropical countries) and corn or maize (U.S. and other temperate countries). The availability of agricultural feedstocks that provide readily fermentable carbohydrates is limited because of competition with food and feed production, arable land usage, water availability, and other factors. Consequently, lignocellulosic feedstocks such as forest residues, trees from plantations, straws, grasses and other agricultural residues are looked to as feedstocks for biofuel production. Unlike utilization of fossil fuels, deriving bioethanol from such plant or even municipal waste sources provides an environmentally sustainable resource for the production of liquid fuels.

A highly efficient route to the production of bioethanol is the gasification of biomass or other organic matter into a substrate gas comprising CO and/or hydrogen followed by the conversion of the gas to ethanol using homoacetogenic microorganisms. Methods for such conversion are known from U.S. Pat. No. 7,285,402 B2, US 20110059499 A1, US 20090215163 A1, and others.

Typically the substrate gas for carbon monoxide or hydrogen conversions is derived from a synthesis gas (syngas) from the gasification of carbonaceous materials, reforming of natural gas and/or biogas from anaerobic fermente4'᷊s or from off streams of various industrial methods. The gas substrate contains carbon monoxide, hydrogen, and carbon dioxide and usually contains other components such as water vapor, nitrogen, methane, ammonia, hydrogen sulfide and the like. (For purposes herein, all gas compositions are reported on a dry basis unless otherwise stated or clear from the context.)

Production of ethanol from the substrate gas by these methods requires significant amounts of hydrogen and carbon monoxide. For instance, the theoretical equations for the conversion of carbon monoxide and hydrogen to ethanol are:

$$6CO+3H_2O.C_2H_5OH+4CO_2$$

$$6H_2+2CO_2.C_2H_5OH+3H_2O$$

As can be seen, the conversion of carbon monoxide results in the generation of carbon dioxide. The conversion of hydrogen involves the consumption of hydrogen and carbon dioxide, and this conversion is sometimes referred to as the $H_2/CO_2$ conversion. For purposes herein, it is referred to as the hydrogen conversion.

Syngas fermentation processes suffer from the poor solubility of the gas substrate, i.e., carbon monoxide and hydrogen, in the liquid phase of the fermentation menstruum. Munasinghe, et al., in *Biomass-derived Syngas Fermentation in Biofuels: Opportunities and Challenges, Biosource Technology,* 101 (2010) 5013-5022, summarize volumetric mass transfer coefficients to fermentation media reported in the literature for syngas and carbon monoxide in various reactor configurations and hydrodynamic conditions. As a result biofermentation processes for the production of ethanol will require large volumes of fermentation liquid. For example commercial scale plants, those with production capacities of 55 million gallons or more, will require fermentation zones that utilize vessels holding a million gallons or more of the fermentation liquid. Moreover, the fermentation processes will need to be operated in a continuous manner for extended periods of time.

To maintain the efficiency of producing ethanol by such fermentation zones there is a need to maximize the production of $C_2$ oxygenated products while minimizing the production of higher carbon chain products such as $C_4$, $C_6$, $C_8$ and higher organic acids or alcohols. The known methods seek to accomplish this efficiency by utilizing homoacetogenic bacteria that have a very high degree of selectivity for the production of $C_2$ products. By their nature the homoacetogenic organisms that convert the gas substrate to ethanol do not have the pathways to make these longer carbon chain products.

The ability of homoacetogenic organisms to survive with minimal media on the CO and $H_2$ substrate under anaerobic condition provides a protection against many biological contaminants that require much different environments. However, the size and scale of the fermentation zones and overall facilities necessary for the production of ethanol on a commercial basis precludes axenic operation of the facilities. As a result microbial contamination will inevitably occur at some point and can degrade the production by producing such higher chain byproducts which in turn severely reduces the yield of ethanol or other desirable products.

While there are many potential contaminants, one common class of potential contaminants will produce butyric acid, butanol and other longer chain organic acids or alcohols. Microorganisms that produce such compounds as part of their primary metabolism are referred to as butyrogens. There are many classes of butyrogens. One major class utilizes carbohydrates and other carbon compounds such as amino acids, lipids, etc. Another class of butyrogens uses syngas and yet another class of butyrogens can utilize ethanol and acetate with transferase enzyme pathways. Since, for the reasons previously mentioned, it is not possible to operate such large fermentation axenically, all of these butyrogen contamination sources will exist.

Once the butyrogen contamination takes hold in a large scale fermentation vessel it can destroy the commercial viability of the process by shifting feed conversion from desired products and making product recovery impractical. Designing product recovery facilities for wide variations in composition and concentration of liquid compounds would add prohibitive cost. The large volume of the fermentation liquid and the time to incubate the microorganisms to production concentrations make flushing and restarting of the facility impractical as well.

In contrast, conventional ethanol plants, such as corn ethanol plants, operate a plurality of batch reactors and thus inherently limit the time that competitive microorganisms have available for population increase. Indeed, often the duration of the batch fermentations is based upon the ethanol titer and the concentration of undesired, higher alcohols. Moreover, the fermenters can be sterilized between batches to eliminate the presence of undesired microorganisms.

Therefore methods are sought to eliminate or inhibit the growth of butyrogens in a large scale fermentation zone without disrupting the ongoing production of ethanol or other products such as acetic acid, propanol, or propionic acid from such a fermentation zone.

SUMMARY

By this invention, a certain class of crotonate-like compounds have been found to inhibit the growth of a butyrogen population while not unduly disrupting the productivity of homoacetogenic or heteroacetogenic microorganisms that produce light oxygenate products such as ethanol, acetic acid, propanol, and propionic acid. Achieving this discovery required the identification that these compounds act as bacteriostatic or bacteriocidal agents to the butyrogens while not unduly inhibiting the growth of the homoacetogens. Whether the compound acts as a bactericide or bacteriostatic agent, its ability to act in vivo is equally important for its effectiveness in preserving production of desired products in a large scale fermentation zone operated on a continuous basis for extended periods of time. The discovered class of compounds was found to be effective in vivo and therefore will act to inhibit or retard butyrogen contamination within the fermentation vessel and may be introduced as an additive in the process as needed. These crotonate-like compounds that act in bacteriocidal or bacteriostatic manner of this invention are referred to herein as butyl retardants.

Effective crotonate-like compounds can be represented by the structural formula $$R^2(R^3)C{=}C(H)C(O)R^1 \qquad \text{I.}$$

or $$R^2\text{-}A\text{-}C(O)R^1 \qquad \text{II.}$$

wherein:

- $R^1$ is —OH, —$OR^5$, or —$N(R^4)_2$, wherein $R^5$ is hydrocarbyl, preferably of 1 to 6 carbons and each $R^4$ may be the same or different and is hydrogen or hydrocarbyl of preferably 1 to 6 carbons;
- $R^2$ is hydrogen, —$NH_2$, —OH or —$CX_3$ wherein each X may be the same or different and is hydrogen or halogen, preferably perhalogenated and most preferably perfluorinated;
- $R^3$ is hydrocarbyl of 1 to 18 carbons which may be unsubstituted or substituted with —OH, alkoxyl of 1 to about 6 carbons, or halogen, preferably perhalogenated and most preferably perfluorinated;
- A is an aromatic moiety having 5 or 6 ring atoms which may be all carbon atoms or may be heterocyclic with one hetero atom selected from the group consisting of oxygen and nitrogen which aromatic moiety has —$R^2$ at the 2 position wherein —$R^2$ is as defined above and which aromatic moiety may be unsubstituted or substituted at one or more of the higher carbon positions (e.g., 3-, 4-, 5- and 6-positions for a phenyl moiety) with (i) hydrocarbyl of 1 to 18 carbons which may be substituted with —OH, alkoxyl of 1 to about 6 carbons, or halogen, (ii) —$OR^6$ wherein $R^6$ is lower alkyl, or (iii) —$N(R^7)_2$ wherein each $R^7$ is the same or different and is hydrogen or hydrocarbyl, preferably of 1 to 6 carbons, or (iv) halogen, preferably fluorine;

with the proviso that in structural formula I, at least one, and preferably both, of $R^2$ and $R^3$ is or is substituted with haloalkyl and that in formula II at least the 2 or 3 carbon position of the aryl moiety is substituted with an electron withdrawing group selected from the group consisting of halogen and haloalkyl. The hydrocarbyl groups are preferably alkyl groups, and most preferably linear or branched alkyls.

The preferred crotonate-like compounds can be represented by the structural formulae:

$$R^2(R^3)C{=}C(H)C(O)R^1 \qquad \text{III.}$$

or $$R^2\text{-}A\text{-}C(O)R^1 \qquad \text{IV.}$$

wherein:

- in formula III, $R^2$ is —OH, —$NH_2$ or —$CX_3$ wherein X is halogen, preferably fluorine, and $R^3$ is —$CX_3$ wherein X is halogen, preferably fluorine, and
- in formula IV, the aryl is phenyl and at least one of the 2 and 3 position carbons of the phenyl moiety is —$CX_3$ wherein X is halogen, preferably fluorine.

While not intended to be in limitation, these preferred crotonate-like compounds share not only similar spatial configurations but also a reduced electron density at the 3 position carbon of formula I and 2 position on the aryl moiety as compared to that of that carbon of crotonate anion. The halogenated substituents are electron withdrawing. The presence of electron donating substituents such as amine, hydroxyl or alkoxy can moderate the effect of electron withdrawing substituents. Hence, in preferred embodiments, where an electron donating substituent is present, a strong electron drawing moiety, such as a perfluoroalkyl, is used.

One class of crotonate-like compounds are di-halogen substituted crotonate compounds (crotonates having two terminal perhalogenated methyl groups). The di-halogen substituted crotonate compounds include acids, amides and esters. Representative compounds include alkyl 4,4,4-trifluoro-3-(trifluoromethyl)crotonate; 4,4,4-trifluoro-3-(trifluoromethyl)crotonic acid; 4,4,4-trifluoro-3-(trifluoromethyl)crotonamide; alkyl 4,4,4-trifluoro-3-(trichloromethyl)crotonate; 4,4,4-trifluoro-3-(trichloromethyl)crotonic acid; 4,4,4-trifluoro-3-(trichloromethyl)crotonamide; alkyl 4,4,4-trichloro-3-(trifluoromethyl)crotonate; 4,4,4-trichloro-3-(trifluoromethyl)crotonic acid; 4,4,4-trichloro-3-(trifluoromethyl) crotonamide; alkyl 4,4,4-trichloro-3-(trichloromethyl) crotonate; 4,4,4-trichloro-3-(trichloromethyl)crotonic acid; 4,4,4-trichloro-3-(trichloromethyl)crotonamide; 4,4,4-tribromo-3-(trifluoromethyl)crotonic acid; 4,4,4-tribromo-3-(trifluoromethyl)crotonamide; alkyl 4,4,4-tribromo-3-(trifluoromethyl)crotonate; 4,4,4-trifluoro-3-(tribromomethyl) crotonic acid; 4,4,4-trifluoro-3-(tribromomethyl) crotonamide; 4,4,4-trichloro-3-(tribromomethyl)crotonic acid; 4,4,4-trichloro-3-(tribromomethyl)crotonamide; 4,4,4- triiodo-3-(trifluoromethyl)crotonic acid; 4,4,4-triiodo-3-(trifluoromethyl)crotonamide; alkyl 4,4,4-triiodo-3-(trichloromethyl)crotonate; 4,4,4-trifluoro-3-(triiodomethyl) crotonic acid; 4,4,4-trifluoro-3-(triiodomethyl)crotonamide; 4,4,4-trichloro-3-(triiodomethyl)crotonic acid and 4,4,4-trichloro-3-(triiodomethyl)crotonamide where alkyl is lower alkyl, preferably of 1 to 4 carbons, especially ethyl.

Another class of crotonate-like compounds are phenyl containing compounds including, but not limited to, 2-trifluoromethylbenzoic acid; 2-trifluoromethylbenzamide; alkyl 2-trifluoromethylbenzoate; 3-trifluoromethylbenzoic acid; 3-trifluoromethylbenzamide; alkyl 3-trifluoromethylbenzoate; 2-amino-3-trifluoromethylbenzoic acid; 2-amino-3-trifluoromethylbenzamide; alkyl 2-amino-3-trifluoromethylbenzoate; 3-trifluoro-4-methoxybenzoic acid; 3-trifluoro-4-methoxybenzamide; alkyl 3-trifluoro-4-methoxybenzoate; 3-trifluoromethyl-4-fluorobenzoic acid; 3-trifluoromethyl-4-fluorobenzamide; alkyl 3-trifluoromethyl-4-fluorobenzoate; 3-trifluoromethyl-5-trifluoromethylbenzoic acid; 3-trifluoromethyl-5-trifluoromethylbenzamide; alkyl 3-trifluoromethyl-5-trifluoromethylbenzoate; 2-trichloromethylbenzoic acid; 2-trichloromethylbenzamide; alkyl 2-trichloromethylbenzoate; 3-trichloromethylbenzoic acid; 3-trichloromethylbenzamide; alkyl 3-trichloromethylbenzoate; 2-amino-3-trichloromethylbenzoic acid; 2-amino-3-trichloromethylbenzamide; alkyl 2-amino-3-trichloromethylbenzoate; 3-trichloro-4-methoxybenzoic acid; 3-trichloro-4-methoxybenzamide; alkyl 3-trichloro-4-methoxybenzoate; 3-trichloromethyl-4-chlorobenzoic acid; 3-trichloromethyl-4-chlorobenzamide; alkyl 3-trichloromethyl-4-chlorobenzoate; 3-trichloromethyl-5-trichloromethylbenzoic acid; 3-trichloromethyl-5-trichloromethylbenzamide; and alkyl 3-trichloromethyl-5-trichloromethylbenzoate where alkyl is lower alkyl, preferably of 1 to 4 carbons, especially ethyl.

Another class of crotonate-like compounds are 3-amino substituted crotonates such as 4,4,4-trifluoro-3-aminocrotonic acid; 4,4,4-trifluoro-3-aminocrotonamide; alkyl 4,4,4-trifluoro-3-aminocrotonate; 4,4,4-trichloro-3-aminocrotonic acid; 4,4,4-trichloro-3-aminocrotonamide; alkyl 4,4,4-trichloro-3-aminocrotonate; 4,4,4-tribromo-3-aminocrotonic acid; 4,4,4-tribromo-3-aminocrotonamide; alkyl 4,4,4-tribromo-3-aminocrotonate; 4,4,4-triiodo-3-aminocrotonic acid; 4,4,4-triiodo-3-aminocrotonamide; and alkyl 4,4,4-triiodo-3-aminocrotonate where alkyl is lower alkyl, preferably of 1 to 4 carbons, especially ethyl.

The effect of the crotonate-like compounds varies with their concentration. In accordance with this invention the crotonate-like compounds will be effective in fermentation process with a concentration of the pure compound of as little as 50 ppm by mass to inhibit the growth of the butyrogens. Effective concentrations may be reduced significantly with the use of delivery systems and agents that improve the distribution in the medium containing the microorganisms and improve uptake of the compounds by the microorganisms. In most cases concentrations in excess of 1000 ppm by mass are avoided so as to not unduly hinder the growth of the microorganisms that are producing the light oxygenates such as ethanol.

A broad aspect of this invention is a method of restricting the production of butyrate and butanol and higher molecular weight analogues (herein after collectively referred to as higher oxygenates) in an anaerobic fermentation of a gas substrate that comprises at least one of CO and/or a mixture of $CO_2$ with hydrogen. The method passes the gas stream to an anaerobic fermentation zone containing at least one species of anaerobic microorganism capable of producing an oxygenated liquid product other than or in addition to higher oxygenates. At least a portion of the gas stream is converted to the liquid product by contact of the microorganism in the fermentation zone with the gas stream. A crotonate-like compound is added to the fermentation liquid as a butyrogenic retardant in an amount effective to restrict production of higher oxygenates. The method withdraws a fermentation liquid containing the liquid product from the fermentation zone and recovers the liquid product from the fermentation liquid. The fermentation zone will usually contain multiple species of microorganisms, typically a homoacetogenic microorganism for the production of a liquid product and a butyrogenic microorganism that produces butyrate and/or butanol. The fermentation zone may also contain heteroacetogenic microorganisms that produce a butyrate or butanol as well as a liquid product such as acetic acid and/or ethanol or propanol.

Another broad aspect of this invention is a method of producing ethanol by the fermentation of a gas stream that contains CO and/or a mixture of $CO_2$ with hydrogen using a homoacetogenic microorganism to convert the gas stream wherein the production of higher oxygenates is inhibited. The method passes the gas stream to a fermentation zone containing a homoacetogenic microorganism and a fermentation liquid. Contact of the homoacetogenic microorganism with the gas stream produces ethanol in the fermentation zone. Crotonate-like compound is introduced into the fermentation liquid in a sufficient amount to inhibit the growth of butyrogens and the production of higher oxygenates. The butyrogenic retardant concentration may range between 10 and 1000 ppm by mass on an intermittent or continual basis. The method withdraws ethanol containing fermentation liquid from the fermentation zone and an ethanol product is recovered from the fermentation liquid.

In another form this invention is a method for producing ethanol by the fermentation of a gas stream that contains CO and/or a mixture of $CO_2$ with hydrogen using a homoacetogenic microorganism to convert the gas stream to ethanol. The method passes the gas stream to a fermentation zone containing the homoacetogenic microorganism and a fermentation liquid that converts the gas stream to ethanol by contact with the homoacetogenic microorganism. A butyrogenic retardant comprising crotonate-like compound is added to the fermentation zone to disrupt the growth of butyrogens. The butyrogenic retardant is added in an amount that produces a concentration of the crotonate-like compound in a range of between 50 and 1000 ppm by mass. The method withdraws the ethanol containing fermentation liquid from the fermentation zone and an ethanol product is recovered from the fermentation liquid. In a preferred form of the invention the butyrogenic retardant comprises at least one of 4,4,4-trifluoro-3-trifluoromethylcrotonic acid; 4,4,4-trifluoro-3-trifluoromethylcrotonamide; ethyl 4,4,4-trifluoro-3-trifluoromethylcrotonate; 4,4,4-trifluoro-3-aminocrotonic acid; 4,4,4-trifluoro-3-aminocrotonamide; ethyl 4,4,4-trifluoro-3-aminocrotonate; 2-trifluoromethylbenzoic acid; 2-trifluoromethylbenzamide; ethyl 2-trifluoromethylbenzoate; 3-trifluoromethylbenzoic acid; 3-trifluoromethylbenzamide; ethyl 3-trifluoromethylbenzoate; 2-amino-3-trifluoromethylbenzoic acid; 2-amino-3-trifluoromethylbenzamide; and ethyl 2-amino-3-trifluoromethylbenzoate; and the crotonate-like compound is added to the fermentation zone at a concentration of 50 to 500 ppm by mass.

Although the methods of this invention provide exceptional value in the anaerobic microbial production of light oxygenates using syngas, the methods still have applicability to other processes for making light oxygenates. Accordingly, another broad aspect of this invention pertains to a method of restricting the production of higher oxygenates by contaminating butyrogens in fermentation processes by providing an effective amount of the certain crotonate-like compounds to the fermentation liquid. In particular, this broad aspect of the invention pertains to an improvement in processes for the metabolic conversion of substrate, which may be one or more of sugar or other carbohydrate or carbon monoxide or hydrogen and carbon dioxide to light oxygenates comprising contacting in a fermentation liquid containing said substrate with microorganisms capable of bioconverting the substrate to light oxygenates under fermentation conditions which may be aerobic or anaerobic, said fermentation liquid being susceptible to the presence of contaminating bacteria capable of producing at least one of butyrate or butanol from said substrate or from said light oxygenates through a butyryl CoA enzyme, wherein the improvement comprises providing in said fermentation liquid a sufficient amount of a crotonate-like compound to restrict the production of higher oxygenates.

FIGURES

DETAILED DESCRIPTION

Definitions

Figure 1:
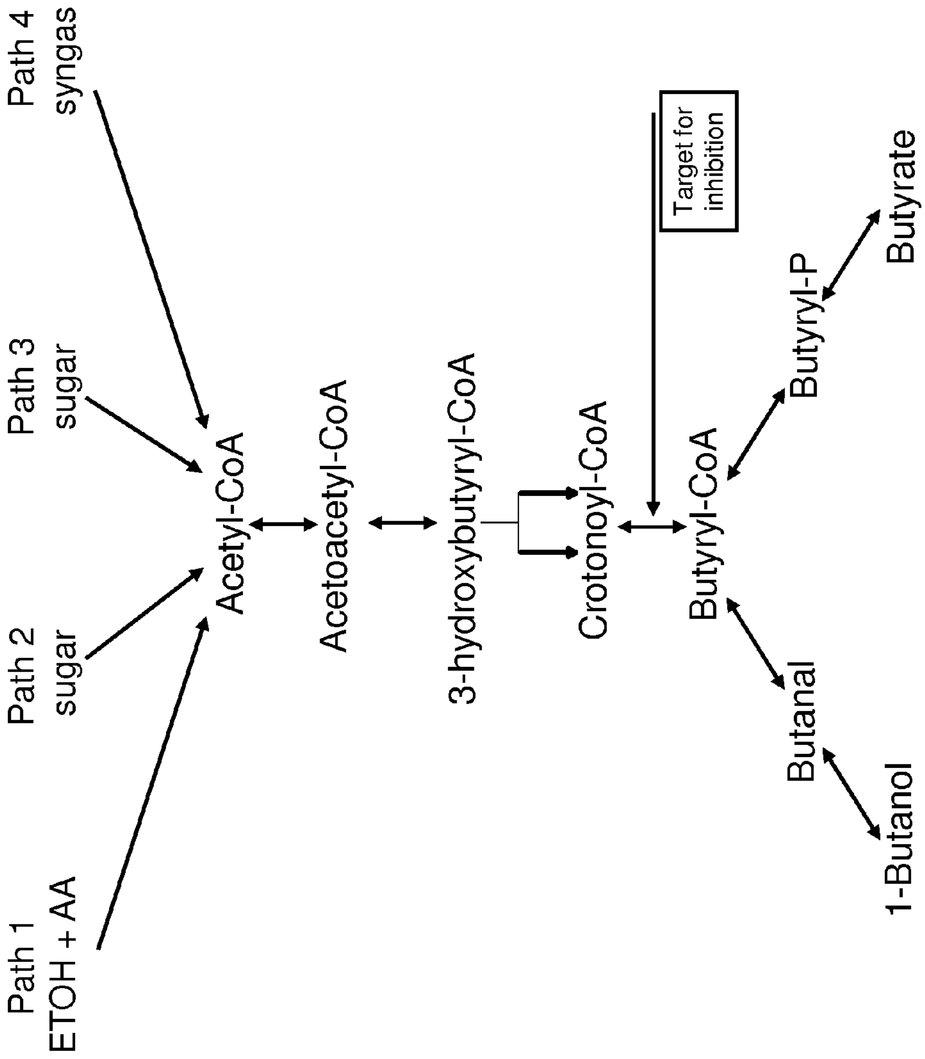
FIG. 1 is diagram illustrating some key enzymes products and intermediate products in butyrogen metabolism for producing butanol and butyrate.

Butyrogens refer to microorganisms that under anaerobic conditions produce compounds having four carbon atoms such as butyrates and butanol and the term can also include microorganisms that produce longer chain ($C_6$-$C_8$) organic acids and alcohols.

Butyrogenic retardant refers to a compound that is used to inhibit or kill the butyrogens. The term contemplates the activity of the compound as a bactericide or bacteriostatic agent.

Butyl impurity refers to any molecule that has a total of four or more carbon atoms in its structure with the carbon atoms arranged as a chain.

Light oxygenates refers to any molecule that has two or three carbon atoms and at least one carbon-oxygen bond.

General Description

This invention applies to anaerobic fermentations to produce light oxygenates such as ethanol, acetic acid, propanol, and propionic acid using a gas substrate comprising carbon monoxide and hydrogen, and the gas will typically contain carbon dioxide and nitrogen. Syngas is one source of such a gas substrate. Syngas can be made from many carbonaceous feedstocks. These include sources of hydrocarbons such as natural gas, biogas, gas generated by reforming hydrocarbon-containing materials, peat, petroleum coke, and coal. Other sources for production of syngas include waste material such as debris from construction and demolition, municipal solid waste, and landfill gas. Syngas is typically produced by a gasifier. Conversion of natural gas to syngas, e.g., by partial oxidation such as disclosed in U.S. patent application Ser. No. 13/304,902, filed Nov. 28, 2011, hereby incorporated by reference in its entirety, is also an attractive source of syngas feedstock. Any of the aforementioned biomass sources are suitable for producing syngas. The syngas produced thereby will typically contain from 10 to 60 mole % CO, from 10 to 25 mole % $CO_2$ and from 10 to 60 mole % $H_2$. The syngas may also contain $N_2$ and $CH_4$ as well as trace components such as $H_2S$ and COS, $NH_3$ and HCN. Other sources of the gas substrate include gases generated by petroleum and petrochemical processing. These gases may have substantially different compositions than typical syngas, and may be essentially pure hydrogen or essentially pure carbon monoxide. Also, the substrate gas may be treated to remove or alter the composition including, but not limited to, removing components by sorption, membrane separation, and selective reaction. Components may be added to the gas substrate such as nitrogen or adjuvant gases such as ammonia and hydrogen sulfide. The term syngas will be used herein and will be intended to include these other gas substrates.

This invention will use homoacetogenic microorganisms and fermentation conditions particularly selected for the production of light oxygenates and preferably selected for the production of ethanol. Bioconversions of CO and $H_2/CO_2$ to acetic acid and ethanol and other products are well known. Suitable microorganisms live and grow under anaerobic conditions, meaning that gaseous and dissolved oxygen is essentially absent from the fermentation zone. A concise description of biochemical pathways and energetics for acetogenic bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds., Springer (2003). Any microorganisms that have the ability to produce ethanol by converting the syngas components: CO, $H_2$, $CO_2$ individually or in combination with each other or with other components that are typically present in syngas may be utilized. Suitable microorganisms and/or growth conditions may include those disclosed in U.S. Pat. No. 7,704,723 entitled "Isolation and Characterization of Novel Clostridial Species," which discloses a biologically pure culture of the microorganism *Clostridium ragsdalei* having all of the identifying characteristics of ATCC No. BAA-622 which is incorporated herein by reference in its entirety. *Clostridium ragsdalei* may be used, for example, to ferment syngas to ethanol.

Suitable microorganisms include: *Clostridium Ljungdahlii*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid; *Clostridium autoethanogemum* sp. nov., an anaerobic bacterium that produces ethanol from carbon monoxide. Jamal Abrini, Henry Naveau, Edomond-Jacques Nyns, Arch Microbiol., 1994, 345-351; Archives of Microbiology 1994, 161: 345-351; and *Clostridium Coskatii* having the identifying characteristics of ATCC No. PTA-10522 filed as U.S. Pat. No. 8,143,037. All of these references are incorporated by reference herein in their entirety.

The invention can provide benefit for any type of fermentation zone. Suitable fermentation zones are typically referred to as a bioreactor. The term "bioreactor" includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Bubble Column, Gas Lift Fermenter, Membrane Reactor such as Hollow Fiber Membrane Bioreactor (HFMBR), Static Mixer, or other vessel or other device suitable for gas-liquid contact.

Typical bioreactors have the arrangement of a suspended cell type bioreactor or membrane supported bioreactor. In a suspended cell type bioreactor the fermentation liquid contains the microorganisms in suspension as the gas substrate passes through the fermentation liquid to effect contacting between the gas and the microorganisms by absorption of the gas into the liquid and uptake of the dissolved gas by the microorganism. Suspended cell bioreactors typically take the form of a continuous stirred tank where impellers provide mechanically mix the gas substrate and the fermentation liquid or a bubble column bioreactor where the injection of the substrate into the gas promotes mixing of the gas and liquid.

A membrane supported bioreactor utilizes a solid surface upon which to grow the microorganisms as a biofilm or a concentration of cells that the substrate gas contacts. One membrane bioreactor, as shown in US 20080305539 A1, grows the biofilm on one side of the membrane and in direct contact with the fermentation liquid while the substrate gas permeates into contact with the biofilm from the opposite side of the membrane. US 20090215163 A1 discloses the opposite arrangement for a membrane supported bioreactor where one side of the membrane retains the microorganisms in direct contact with the gas substrate while the fermentation liquid permeates from the opposite of the membrane and into contact with the microorganisms. Either type of membrane supported bioreactor is suitable for use with this invention.

When using the invention with a suspended cell bioreactor the fermentation liquid will include a suspension of microorganisms and various media supplements. The various adjuvants to the fermentation liquid may comprise buffering agents, trace metals, vitamins, salts etc. Adjustments in the fermentation liquid may induce different conditions at different times such as growth and non-growth conditions which will affect the productivity of the microorganisms. Previously referenced U.S. Pat. No. 7,704,723, the contents of which are hereby incorporated by reference, discloses the conditions and contents of suitable fermentation menstruum for bioconversion of CO and $H_2/CO_2$ using anaerobic microorganisms. Other methods, operating conditions and media for operating bioreactors to produce ethanol are described in the literature that includes those described in WO2007/117157, WO2008/115080, U.S. Pat. No. 6,340,581, U.S. Pat. No. 6,136,577, U.S. Pat. No. 5,593,886, U.S. Pat. No. 5,807,722 and U.S. Pat. No. 5,821,111, each of which is incorporated herein by reference.

The fermentation is carried out under appropriate conditions that include pressure, temperature, gas flow rate, liquid flow rate, media pH, media redox potential, agitation rate (if using a continuous stirred tank reactor), inoculum level, and maximum gas substrate concentrations to ensure that CO in the liquid phase does not become limiting, and maximum product concentrations to avoid product inhibition. Suitable conditions are described in WO02/08438, WO07/117,157 and WO08/115,080. Typically, the fermentation liquid and the microorganisms in the fermentation zone include a suitable temperature in the range of between 25° C. and 60° C., and more frequently in the range of about 30° C. to 40° C. Other conditions of fermentation include the density of microorganisms, fermentation liquid composition, and liquid depth, which are all preferably sufficient to achieve the sought conversion of hydrogen and carbon monoxide.

Fresh liquid media containing nutrients will typically enter the bioreactor on a continual basis. The addition of the fresh media and the withdrawal of fermentation liquid provide a continual withdrawal of cell mass from the bioreactor. As the fermentation continues to generate cell mass, the removal and addition rate of media and fermentation liquid will establish a mean cell retention time in the bioreactor. Mean cell retention times for most fermentation zones are typically in a range of from 2 to 7 days.

The butyrogenic retardant as described in this invention is a class of compounds that has the effect of inhibiting or stopping the production of acids or alcohols with four or longer chain carbon atoms by microorganisms in a fermentation zone while not substantially interfering with the conversion of syngas to lower carbon number oxygenates such C2 and C3 acids and alcohols. Useful butyrogenic retardants are any compounds that can interfere with the butyl impurity production of one or more butyrogens. Known butryrogens include the strict butyrogens that produce essentially only butyl impurities and heteroacetogens that can produce ethanol and acetate along with butyl impurities.

Butryrogens are characterized by having a critical step of in their metabolic pathway for the conversion of crotonyl-CoA to butyryl-CoA. FIG. 1 shows generalized pathways for butyrogen metabolism and that the pathways for production of butanol and butyrate differ only in the starting substrates. The starting substrates to the production of butanol and butyrate include ethanol and acetic acid through path 1, sugar through path 2 and 3, and syngas through path 4.

Butyrogens such as *C. acetobutylicum*, make butyrate as a primary product or as a smear of short-chain fatty acid products as part of their primary metabolism in which several acids and their corresponding solvents are also produced (FIG. 1, Path 2). These organisms use sugars or proteins as substrates for metabolite production. Other butyrogens, such as various *Eubacterium* strains and *Roseburia* are strictly butyrogenic and produce large amounts of the acid by using a different enzyme to generate the final product, butyrate (FIG. 1, Path 3). These classes of butyrogens are predicted to be less problematic than those that use Path 1 and Path 4 since they may be metabolically disadvantaged under the growth conditions predicted to exist in large-scale syngas reactors.

Path 1 (FIG. 1) encompasses *C. kluyveri* and similar metabolic types of organisms that can use ethanol, acetate and hydrogen to make $C_4$ and higher chained acids. *C. kluyveri* can reside in a reactor and form a commensal relationship with other organisms, thus potentially making it metabolically advantaged and which can lead to persistent infections if the fermenter's environmental conditions are not altered. Thus, of the non-syngas using butyrogens, *C. kluyveri* and similar types pose a high risk for long-term, persistent contamination since they can readily make $C_4$ or higher acids from ethanol and acetate or two acetates. This reaction is also thermodynamically advantaged under certain conditions.

Finally, organisms that use Path 4 (FIG. 1) are those that can grow on both sugars and syngas and produce a variety of short chain and higher chain acids and alcohols. These are broadly classified as the heteroacetogens and members include *C. carboxidivorans* and *C. drakei*. These heteroacetogens can use either sugars as well as syngas substrates and can also make $C_4$ acids and solvents from $C_2$ subunits. The heteroacetogens pose a slightly higher risk than other butyrogens, since they may be metabolically advantaged under the low redox, high dissolved syngas conditions that would exist in a large-scale fermentation zone.

As with the strict butyrogens, the heteroacetogens use a common pathway to generate $C_4$ compounds. The entry point into butyrogenesis, which is a highly conserved pathway except for a few endpoint reactions among all butyrogens, occurs when two acetyl-CoAs condense to form acetoacetyl-CoA by a reaction with thiolase. This is followed by a hydroxylation at one of the carbonyls to form S3-hydroxybutyryl-CoA (FIG. 1). Hydroxybutyryl-CoA is dehydrated by crotonase to form crotonyl-CoA. The previous reaction to form 3-HBCoA can be achieved by a variety of dehydrogenases and does not generate any energy for the cell, but it does regenerate some oxidized cofactor. Once the crotonyl-CoA is generated the cell becomes susceptible to inhibitors since most, if not all, of the energy derived from butyrogenesis comes from the conversion of crotonyl-CoA to butyryl-CoA. All of these pathways could be stopped by disrupting the critical step of converting the crotonyl CoA to butyryl CoA.

It was found that a class of crotonate-like compounds described above would act as butyl retardants in the production of light oxygenates from syngas. While not wishing to be limited to theory, it is believed that these compounds interrupt this critical step in the butyrogen metabolism. At the same time, this crotonate-like compounds did not unduly interfere with the production of light oxygenates such as ethanol by a homoacetogen. Importantly, the deleterious effect on the butyrogen occurs in vivo thereby making this retardant suitable for direct use in fermentations.

Although not wishing to be bound by any theory, the crotonate-like compounds used in this invention mimic the unsubstituted crotonate anion but due to electron withdrawing groups affecting the 3 position carbon atom (2 position on the aryl moiety of formula II), and the reduced electron density is involved in the mechanisms interrupting this step.

These butyl retardants often provide desirable results at a relatively low concentration levels. At concentrations as low as 50 ppm by mass in a continuous fermentation the crotonate derivatives had beneficial effects on reducing butanol and butyric acid while not unduly disrupting the production of acetic acid and ethanol. In fact it has been discovered that many crotonate-like compounds of this invention do not begin to unduly affect homoacetogen growth until reaching concentrations of 1000 ppm by mass in the fermentation liquid. Thus, the amount of these crotonate-like compounds added to the fermentation zone can be adjusted to maintain it in a range that will effectively retard the growth of the butyrogens without unduly inhibiting the growth of desired homoacetogens. As a result use of the butyl retardant can be tuned to curtail the production of butyl impurities while not unduly harming the production of ethanol, acetic acid and other light oxygenate products.

The butyl retardant may be added to a fermentation zone in a variety of ways. It may be injected in a desired dosage directly into the fermentation zone. The butyl retardant may also be mixed with the fresh media input or a recycle stream from the fermentation zone to promote better mixing of the butyl retardant in the fermentation zone.

These butyl retardants are readily miscible in simple hydrocarbons and other non-aqueous solvents. For example common aromatic hydrocarbons such as xylenes, toluene etc. or aliphatic hydrocarbons such as hexane dissolve these butyl retardants. Hence the butyl retardant can be dissolved in such hydrocarbon and other non-aqueous solvents and made into microemulsions by well-known techniques by addition of suitable surfactants and cosolvents. These microemulsion particles are typically 0.1 micron in diameter and can be readily dispersed into the fermentation medium. In the fermentation medium, the emulsion particles will contact the butyrogens and deliver the butyl retardants to the organisms. The major advantage of such microemulsion delivery system is that they are effective in much lower dosages because they can protect the active compounds such as the butyl retardant and also assist in delivering the butyl retardant to the cell surface which is the primary target. Methods for making such microemulsions and their usage in general biocide formulations have been described in U.S. Pat. No. 6,096,225 by Yang et al. In a suspended cell or planktonic type fermentation the butyl retardant will be effective when introduced as a single dose at a concentration of from 10 to 1000 ppm by mass with concentration levels of 50 to 500 ppm by mass being preferred for most applications. The effective concentrations will be influenced by the delivery system with microemulsion systems having effective concentration below 50 ppm mass and down to 10 ppm mass or lower. Preferably, where the butyrogenic effect is sought on a continuous basis these dosages are calculated based on the mean cell retention time of the bioreactor such that the dosage will have a duration of at least 2 days. Higher dosage levels may be used on a one time basis for a fermentation operation where the population of butyrogens has is undesirably high in order to bring the population to an acceptable, steady-state level. Although the higher concentration may result in some population loss of homoacetogens, the homoacetogens can quickly regain the desired cell density. Thus even where some loss of homoacetogens may occur, the processes of this invention offer a much more economically viable approach to the control of butyrogens than a cleaning and sterilization of the fermenter.

It is possible to add the butyl retardants in varied amounts in response to monitoring of butyl impurity production and the $C_2$ product output and making adjustments in addition and concentration depending upon the production of the butyl impurities. In this respect the desired amount of butyl retardant can be added to maintain a desired concentration in a fermentation zone or in response to monitoring the presence of butyrogen contamination. Thus, the butyl retardant may be used continually or intermittently to prevent or reverse the effect of butyrogen growth. If desired, the butyl retardant may be added at the start of the of a fermentation process. In this manner the butyl retardant acts as a prophylactic measure to prevent butylrogen contamination from taking hold in the fermenter. The addition may be continued throughout the fermentation process by continuous or intermittent injection of the butyl retardant into the fermentation zone. In such cases a relatively low butyl retardant dosage can be effective. In particular, intermittent dosages at a concentration level of 50 ppm mass or preferably 50 to 100 ppm mass on a frequency of 5 to 10 days may be used. In the absence of recovery and recirculation of liquid containing the butyl retardant, the butyl retardant will wash out of the fermenter at a rate determined by the mean cell retention time.

Regardless of the delivery system any method may be used to determine the presence of butyrogens and the effectiveness of the butyl retardant. Monitoring of the product output for the presence of butyl impurities from the fermentation zone can provide an indication of butyrogen contamination. Preferably the fermentation liquid will undergo periodic sampling for detection of butyl impurities.

Most often the butyl retardant is added in response to the detection of the butyrogens. In this case the butyl retardant is added in sufficient amount to produce a single dose in a concentration of 100 to 1000 ppm by mass in the fermenter, with a dose in the range of 500 to 1000 ppm by mass being preferred. A desired concentration of crotonate-like compound may be maintained until the presence of the butyrogens has been reduced to a desired level as typically indicated by the production of butyl impurities from the fermentation zone. Once sufficient butyrogens have been reduced to a level that produces an acceptable fermentation zone product, the crotonate compound can be allowed to wash out of the fermentation zone.

The butyl retardant can be introduced to achieve a desired reduction in the amount of butyl impurities. Ideally, the butyl impurities in the in the fermentation liquid are reduced to zero, however, the fermentation liquid will typically contain some amount of butyl contamination. In most cases the butyl retardant will be used as necessary to keep the butyrate and butanol concentration in the ethanol containing fermentation liquid below 0.1% and preferably below 0.01%.

EXAMPLES

Examples 1-5

A variety of crotonate-like compounds were tested for their bactericide or bacteriostatic activity. The tested compounds are identified in Table 1.

TABLE 1

| Tested Compounds | | |
|---|---|---|
| A. | ethyl 4,4,4-trifluoro-3-(trifluoromethyl)crotonate | 236.12 |
| B. | ethyl-3-amino-4,4,4-trifluorocrotonate | 182.14 |
| C. | Tert-butyl crotonate (comparative) | 142.20 |
| D. | 4,4,4-trifluoro-3-(trifluoromethyl)crotonic acid | 208.06 |
| E. | ethyl 4,4,4-trifluorocrotonate | 168.12 |
| F. | ethyl-2-methyl-4,4,4-trifluorocrotonate (comparative) | 197.16 |
| G. | 4,4,4-trifluorocrotonic acid | 140.06 |
| H. | ethyl 3-aminocrotonate | 129.16 |

Example 1

These compounds were first tested to determine their effect on a known homoacetogen. Each compound was tested in a series of batch experiments to determine the growth response of a homoacetogen to the presence of the compound at varying concentrations. The batch experiments were all conducted by anoxically filling a Balch tube with 5 ml of a fermentation medium having the composition given in Tables 2 and 3. To expedite results, these batch experiments used fructose as the growth nutrient source for bacteria. Thus, the media included a 5 g/L of fructose.

TABLE 2

Fermentation Medium Compositions

| Components | Amount per liter |
|---|---|
| Mineral solution, See Table 3(a) | 25 ml |
| Trace metal solution, See Table 3(b) | 10 ml |
| Vitamins solution, See Table 3(c) | 10 ml |
| Yeast Extract | 0.5 g |
| Adjust pH with NaOH | 6.1 |
| Reducing agent, See Table 3(d) | 2.5 ml |

TABLE 3(a)

Mineral Solution

| Components | Concentration (g/L) |
|---|---|
| NaCl | 80 |
| $NH_4Cl$ | 100 |
| KCl | 10 |
| $KH_2PO_4$ | 10 |
| $MgSO_4$•$7H_2O$ | 20 |
| $CaCl_2$•$2H_2O$ | 4 |

TABLE 3(b)

Trace Metals Solution

| Components | Concentration (g/L) |
|---|---|
| Nitrilotriacetic acid | 2.0 |
| Adjust the pH to 6.0 with KOH | |
| $MnSO_4$•$H_2O$ | 1.0 |
| $Fe(NH_4)_2(SO_4)_2$•$6H_2O$ | 0.8 |
| $CoCl_2$•$6H_2O$ | 0.2 |
| $ZnSO_4$•$7H_2O$ | 1.0 |
| $NiCl_2$•$6H_2O$ | 0.2 |
| $Na_2MoO_4$•$2H_2O$ | 0.02 |
| $Na_2SeO_4$ | 0.1 |
| $Na_2WO_4$ | 0.2 |

TABLE 3(c)

Vitamin Solution

| Components | Concentration (mg/L) |
|---|---|
| Pyridoxine•HCl | 10 |
| Thiamine•HCl | 5 |
| Roboflavin | 5 |
| Calcium Pantothenate | 5 |
| Thioctic acid | 5 |
| p-Aminobenzoic acid | 5 |
| Nicotinic acid | 5 |
| Vitamin B12 | 5 |
| Mercaptoethanesulfonic acid | 5 |
| Biotin | 2 |
| Folic acid | 2 |

TABLE 3(d)

Reducing Agent

| Components | Concentration (g/L) |
|---|---|
| Cysteine (free base) | 40 |
| $Na_2S$•$9H_2O$ | 40 |

Each tube was inoculated with 0.5 ml of the same strain of *C. autoethanogenum* bacteria seed culture inoculum. The tubes were maintained at a temperature of 37° C. Twenty one hours after the inoculation of the tube with the bacteria, the different crotonate derivatives from Table 1 were added to different tubes in the amounts indicated in Table 4 This was at a time of early to mid-log phase growth for the bacteria. Each fermentation of the bacteria in the media at the different concentration of crotonate derivatives were allowed to progress and were monitored to determine the bacteria growth at selected intervals of time varying from approximately 20 hours to 190 hours. Growth at the intervals was measured by reading the optical density (OD) of the fermentation liquid. Optical density was measured using a Spectronic Spec 20 (Thermo Spectronic) at a wavelength of 600 nm. The OD of the Balch tube culture was measured directly in the tube using absorbance mode on the Spec 20 machine. The machine was set to zero absorbance by first measuring and adjusting the setting to zero absorbance using media only as a blank. This process was repeated at each indicated time point throughout the experiment. The ability of a tube fermentation at a particular concentration of crotonate derivative to reach a predetermined optical density was recorded in Table 4. Table 4 indicates the presence of bacterial growth to an OD of approximately 2 or above with a "+", and to an optical density in a range of 0.5 to 1.5 as a "+/−", and indicates the failure of bacterial growth to reach an optical density of approximately 0.5 as a "−".

TABLE 4

Optical density valuation of *C. autoethanogenum* in response to varying concentrations of crotonate and crotonate-like compounds

| ppm(m) | 0 | 1 | 5 | 10 | 50 | 100 | 500 | 1000 | 5000 | 10000 |
|---|---|---|---|---|---|---|---|---|---|---|
| A | + | + | + | + | + | + | + | + | − | − |
| B | + | + | + | + | + | + | + | + | +/− | − |
| C | + | | | + | | + | + | + | + | − |
| D | + | | | + | | + | + | +/− | − | − |
| E | + | | | + | | + | + | + | − | − |
| F | + | | | + | | + | + | + | +/− | − |
| G | + | | | + | | + | + | +/− | − | − |
| H | + | | | + | | + | + | + | + | + |

As the Table 4 indicates, the homoacetogenic bacteria tolerated the presence of the tested crotonyl compounds up to concentrations of about 5000 ppm.

Example 2

Compounds A and D were again tested to determine their effect on another known homoacetogen. Each compound was tested in a series of batch experiments to determine the growth response of the homoacetogen to the presence of the compound at varying concentrations. These batch experiments were again all conducted by anoxically filling a Balch tube with 5 ml of a fermentation medium having the composition given in Tables 2 and 3. To expedite results, these batch experiments used fructose as the growth nutrient source for bacteria. Thus, the media included 5 g/L of fructose.

Each tube was inoculated with 0.5 ml of the same strain of *C. coskatii* bacteria seed culture inoculum. The tubes were maintained at a temperature of 37° C. Twenty one hours after the inoculation of the tube with the bacteria, the different crotonate derivatives from Table 1 were added to different tubes in the amounts indicated in Table 5. This was at a time of early to mid-log phase growth for the bacteria. Each fermentation of the bacteria in the media at the different concentration of crotonate derivatives were allowed to progress and were monitored to determine the bacteria growth at selected intervals of time varying from approximately 20 hours to 50 hours. Growth at the intervals was determined by measurement of the OD in the manner described in Example 1. The ability of a tube fermentation at a particular concentration of crotonate derivative to reach a predetermined optical density was recorded in Table 5. Table 5 indicates the presence of bacterial growth to an OD of approximately 1.6 or above with a "+". All the samples of *C. Coskatii* reached a relatively high OD after a time of only 50 hours.

TABLE 5

Optical density valuation of *C. coskatii* in response to varying concentrations of crotonate and crotonate-like compounds

| ppm(m) | 0 | 100 | 500 | 1000 |
|---|---|---|---|---|
| A | + | + | + | + |
| D | + | + | + | + |

Example 3

Similar experiments were conducted to make a preliminary determination as to which of the crotonate and crotonate-like compounds would act as butyrogen retardants. For this purpose the selected compounds were tested again in a series of batch experiments to determine the growth response of butyrogens to the presence of the compound at varying concentrations. The batch experiments were all conducted by anoxically filling a 20 ml Balch tube with 5 ml of a fermentation medium having the composition given in Tables 2 and 3. The media included 0.5 v/v final concentration of a fructose substrate. For each of the crotonate concentrations tested, duplicate test tubes were prepared.

Each tube was inoculated with 0.5 ml seed culture inoculum of the strict butyrogen *Clostridium tyrobutyricum*. The tubes were maintained at a temperature of 37° C. Twenty one hours after the inoculation of the tube with the bacteria, the different compounds from Table 1 were added to different tubes in the amounts indicated in Table 6. This was at a time of early to mid-log phase growth for the bacteria. Each fermentation of the bacteria in the media at the different concentration of crotonate derivatives were allowed to progress and were monitored to determine the bacteria growth at selected intervals of time varying from approximately 20 hours to 54 hours. Growth at the intervals was measured by reading the optical density (OD) of the fermentation liquid. Optical density was measured as described in Example 1. The ability of a tube fermentation at a particular concentration of crotonate derivative to reach a predetermined optical density was recorded in Table 6. Table 6 indicates the presence of bacterial growth to an OD of approximately 1.8 or above with a "+", and to an optical density in a range of 0.7 to 1.5 as a "+/−", and indicates the failure of bacterial growth to reach an optical density of approximately 0.7 as a "−".

TABLE 6

Optical density valuation of *C. tyrobutyricum* in response to varying concentrations of crotonate and crotonate-like compounds

| ppm(m) | 0 | 100 | 500 | 1000 |
|---|---|---|---|---|
| A | + | + | +/− | − |
| B | + | + | + | + |
| C (comp) | + | + | + | + |
| D | + | + | + | + |
| E | + | + | + | + |
| F (comp) | + | + | + | + |
| G | + | + | + | + |

Example 4

Similar experiments were conducted to determine the effect of the crotonate derivatives on heteroacetogenic bacteria. Selected crotonate derivatives were tested in a series of batch experiments to determine the growth response of butyrogens to the presence of the compounds at varying concentrations. The batch experiments were all conducted by anoxically filling a 20 ml Balch tube with 5 ml of a fermentation medium having the composition given in Tables 2 and 3. The media included 0.5 v/v final concentration of a fructose substrate. For each of the crotonate concentrations tested, duplicate test tubes were prepared.

Each tube was inoculated with 0.5 ml of the heteroacetogenic bacteria *Clostridium carboxydivorans*. The tubes were maintained at a temperature of 37° C. At a time 20 hours after the inoculation of the bacteria different crotonate derivatives from Table 1 were added to different tubes in the amounts indicated in Table 7. This was at a time of early to mid-log phase growth. Each fermentation of the bacteria in the media at the different concentration of crotonate derivatives were allowed to progress and were monitored to determine the bacteria growth at selected intervals of time varying from approximately 20 hours to 54 hours. Growth at the different intervals was measured by reading the optical density (OD) of the fermentation liquid. Optical density was measured as described in Example 1. The ability of a tube fermentation at a particular concentration of crotonate derivative to reach a predetermined optical density was recorded in Table 7. Table 7 indicates the presence of bacterial growth to an OD of approximately 1.8 with a "+". For these experiments the +/− indicates that one duplicate test tube showed a + indication and the other showed an optical density of less than 0.5.

TABLE 7

Optical density valuation of *C. carboxidivorans* in response to varying concentrations of crotonate and crotonate-like compounds

| ppm(m) | 0 | 100 | 500 | 1000 |
|---|---|---|---|---|
| A | + | + | + | + |
| D | + | + | + | +/− |

Figure 2:
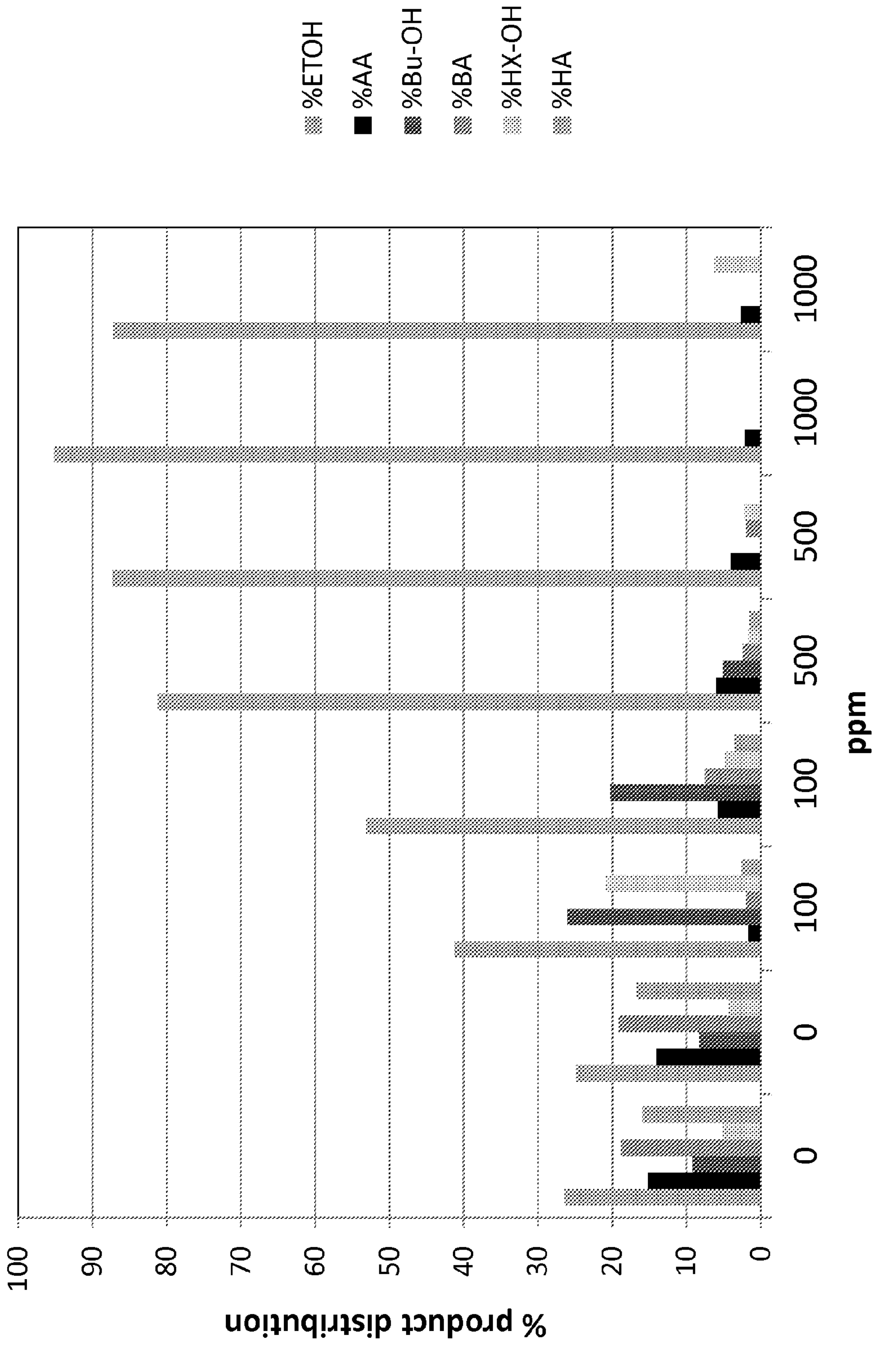
FIG. 2 is a bar graph showing the product distribution from fermentations with heteroacetogenic bacteria in the presence of varying concentrations of a crotonate derivative.

Product profiles were determined on the *C. carboxidivorans* cultures that grew in the presence of compound A. A GC-MSD was performed on 54 hour cultures and product distributions were calculated based on the resultant areas of the output (See FIG. 2). In cultures with no compound A addition, the distribution of $C_2$, $C_4$ and $C_6$ acids and alcohols was similar in both samples. As the compound A concentration increased the amount of $C_2$, particularly the alcohols, increased. At 500 and 1000 ppm virtually all the product observed was the $C_2$ alcohol. Thus the presence of compound A shows the inhibitory effect on $C_4$ and longer chain alcohol and acid production. Thus, such crotonate derivatives can effectively limit the amount of butyl impurity accumulation in the fermentation zone from heteroacetogens which can compete effectively in syngas cultures with homoacetogenic bacteria.

Example 5

Compound A was tested again in set of experiments in all respects the same as that described for Example 4 except that compound A was added to Balch tubes in the amounts indicated in Table 7 at a time 5.5 hours after the inoculation of the bacteria. This was at a time in early log phase growth. In this case the Balch tube that contained no compound A reached an OD of 2 after 29 hours or less. After about 54 hours the tube fermentations that received 100 ppm of compound A had one tube reach an OD of at least 2 while the duplicate tube failed to reach an OD of 1. For all the fermentation tubes that received 500 and 1000 ppm of compound A, the OD failed to rise above about 0.5.

Examples 1-5 showed that compounds A and D were both tolerated by the homoacetogens at concentration of up to 1000 ppm. Both of compounds A and D showed inhibition effect for reducing butyrogen growth. Thus, these dihalogenated crotonyl esters and acids were shown to have useful in-vivo inhibition effects for reducing butyl impurities in homoacetogenic fermentations for the production of ethanol and acetic acid.

Examples 6-10

Additional experiments were conducted to determine the effect of the crotonyl derivatives in continuous fermentations containing butyrogen contamination. Compounds A and D were tested in a 2-L fermenter containing a seed culture from a 10,000 gallon bioreactor used in a large scale fermentation run. The large scale fermentation run had a fermentation liquid volume of approximately 8,000 gallons. The large scale fermentation run was grown from an inoculation of *Clostridium autoethanogenum* that showed a significant presence of buytrogen by the presence of 0.5% butyl compounds in its products.

Figure 3:
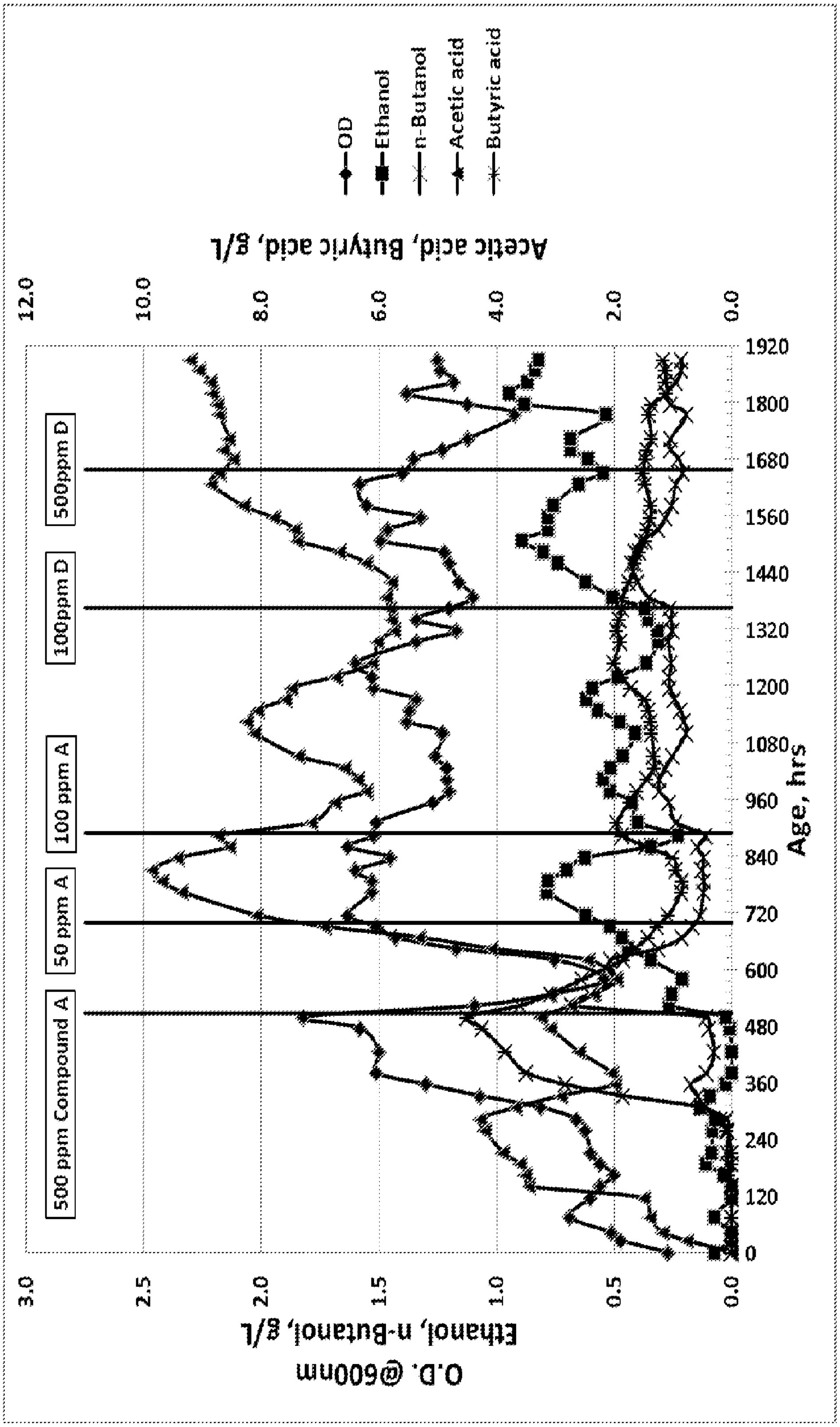
FIG. 3 is a plot showing the concentration of acetate and butyrate compounds over time in a continuous fermenter run along with the optical density of the fermentation liquid.

To initiate the 2 liter fermentation a seed culture from the large scale fermenter was introduced into the 2 liter fermenter and grown on yeast extract to an OD greater than 1 at which time a substantial production of butyrogens was observed. The 2 liter fermenter was a Sartorius Biostat B Series fermenter that operated as a continuously stirred tank with a mixing speed of 200 rpm. After 24 hours of initial growth a gas stream having a composition 38% CO, 38% H2, 15% $C0_2$ and the balance $CH_4$ was introduced into the fermenter. The fermentation was conducted at a temperature of 37° C., a pH of 5.30±0.05 and contained approximately 2 liters of fermentation media having a composition found in Table 8. Fresh fermentation media was continually added to the 2 liter fermenter at rate sufficient to establish a mean cell retention time of 5.8 days. The fermentation was allowed to progress and different concentrations of the compounds A and D were added to the fermentation as intermittent injections at different times. Each injection was allowed to wash out of the fermenter before next injection. The presence of acetate and butyrate compounds in the fermenter along with the OD of the fermentation media are shown in FIG. 3.

TABLE 8

2-liter Fermentation Medium Composition

| Components | Amount per liter |
|---|---|
| Mineral solution, See Table 7(a) | 25 ml |
| Trace metal solution, See Table 7(b) | 10 ml |
| Vitamins solution, See Table 7(c) | 10 ml |
| Yeast Extract | 0 g |
| Adjust pH with NaOH | 6.1 |
| Reducing agent, See Table 2(d) | 2.5 ml |

TABLE 7(a)

Mineral Solution

| Components | Concentration (g/L) |
|---|---|
| NaCl | 0 |
| $NH_4Cl$ | 100 |
| KCl | 10 |
| $KH_2PO_4$ | 20 |
| $MgSO_4•7H_2O$ | 5 |
| $CaCl_2•2H_2O$ | 2 |

TABLE 7(b)

| Trace Metals Solution | |
|---|---|
| Components | Concentration (g/L) |
| Nitrilotriacetic acid | 0 |
| pH 2.0 with 12.1N HCL | |
| $MnSO_4•H_2O$ | 0.377 |
| $Fe(NH_4)_2(SO_4)_2•6H_2O$ | 0 |
| $CoCl_2•6H_2O$ | 0.358 |
| $ZnSO_4•7H_2O$ | 1.96 |
| $NiCl_2•6H_2O$ | 0.078 |
| $Na_2MoO_4•2H_2O$ | 0 |
| $Na_2SeO_4$ | 0.1 |
| $Na_2WO_4$ | 0.118 |
| Fe(SO4)•7H2O | 3.657 |
| pH 2.0 with 12.1N HCL | |

TABLE 7(c)

| Vitamin Solution | |
|---|---|
| Components | Concentration (mg/L) |
| Pyridoxine•HCl | 0 |
| Thiamine•HCl | 10 |
| Riboflavin | 0 |
| Calcium Pantothenate | 10 |
| Thioctic acid | 0 |
| p-Aminobenzoic acid | 0 |
| Nicotinic acid | 0.5 |
| Vitamin B12 | 0 |
| Mercaptoethanesulfonic acid | 0 |
| Biotin | 5 |
| Folic acid | 0 |

TABLE 7(d)

| Reducing Agent | |
|---|---|
| Components | Concentration (g/L) |
| Cysteine (free base) | 40 |
| $Na_2S•9H_2O$ | 0 |
| Clerol antifoam | 0.02 |

Example 6

Figure 4:
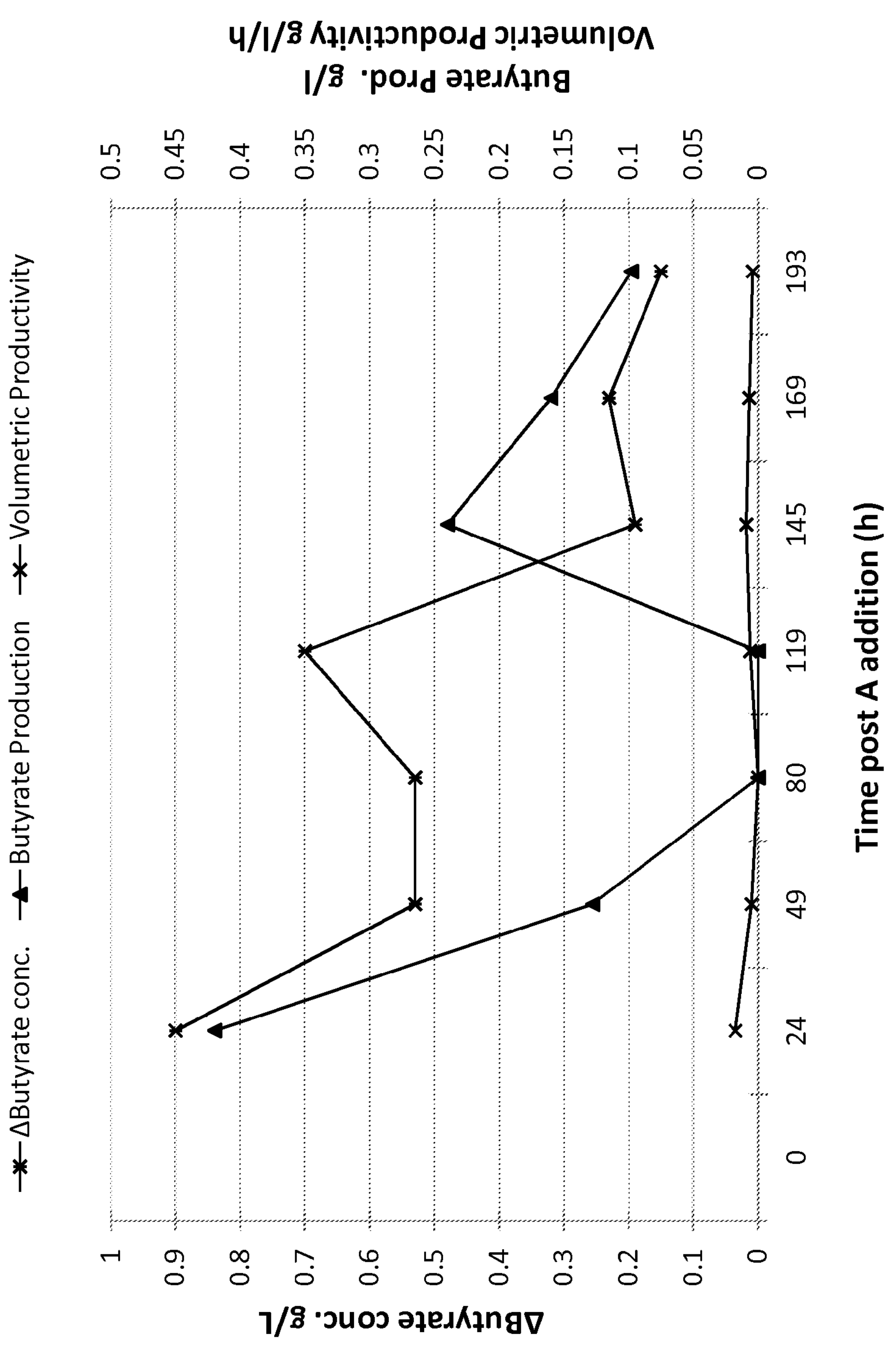
FIG. 4 is a plot showing the production and production rate of butyrate compounds over a selected time period from the continuous fermenter run of FIG. 3.
Figure 5:
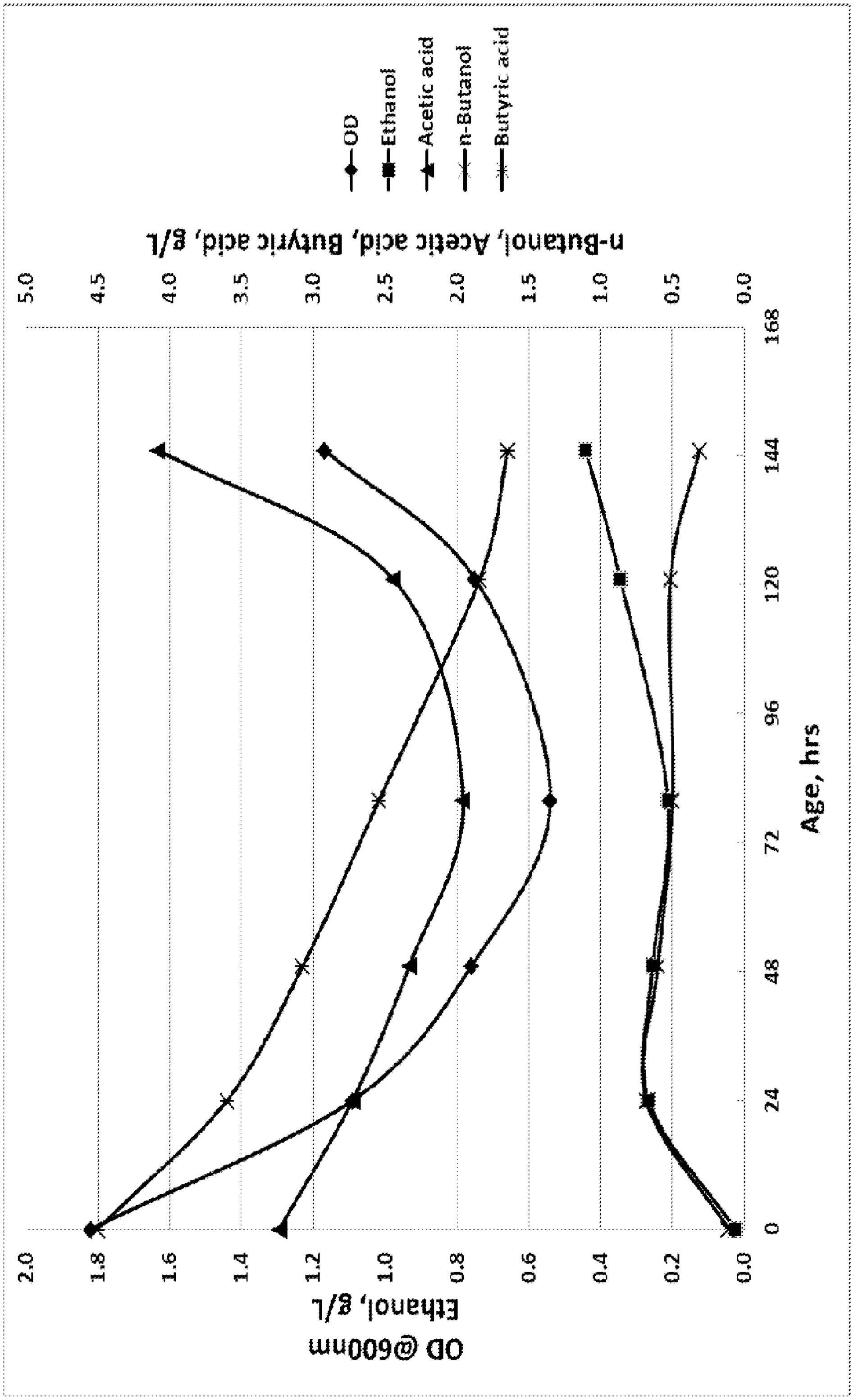
FIG. 5 is an expanded portion of the plot of FIG. 3 between approximately 500 hours and 640 hours.

After approximately 500 hours of fermenter operation compound A was added directly into the fermenter to a concentration of 500 ppm when the OD was 1.82 and butyrate concentration was 4.5 g/L. Following introduction of the compound, the OD decreased rapidly by almost 50% in the first 24 hours and the butyrate concentration decreased by 20% in the same time period. Also in the first 24 hours the butanol content increased rapidly by 6-fold to 0.68 g/L, indicating rapid conversion of the butyric acid to butanol. The rate of conversion of the butyric acid and the dilution rate of the media combined to dramatically decrease the butyrate production rate until it was brought down to zero within 80 hours of initially adding compound A. (See FIG. 4) In addition the OD continued to decrease to a low of 0.54 after 80 hours. Approximately 140 hours after the 500 ppm addition of compound A the OD nearly recovered to its original level with an increase in ethanol of over 100% and a dramatic rise in acetic acid production. (See FIG. 5) The concentration of the $C_2$ and $C_4$ alcohols and acids are shown in Table 9.

TABLE 9

| Addition Hr | OD @600 nm | Ethanol g/L | Acetic acid g/L | n-Butanol g/L | Butyric acid g/L |
|---|---|---|---|---|---|
| 0.0 | 1.82 | 0.026 | 3.237 | 0.109 | 4.503 |
| 24.0 | 1.09 | 0.266 | 2.728 | 0.681 | 3.600 |
| 49.0 | 0.76 | 0.255 | 2.333 | 0.601 | 3.074 |
| 80.0 | 0.54 | 0.212 | 1.959 | 0.497 | 2.542 |
| 121.0 | 0.75 | 0.345 | 2.446 | 0.513 | 1.842 |
| 145.0 | 1.17 | 0.441 | 4.082 | 0.311 | 1.645 |

Example 7

After approximately 700 hours of fermenter operation and the washout of the first 500 ppm addition of compound A, another 50 ppm of compound A was added directly into the fermenter. A decrease in OD and butyrate concentration (See FIG. 3) followed the 50 ppm addition and continued for at least for the first 3 days. At the same time there was a continued increase in the concentration of ethanol and acetic acid.

Example 8

After approximately another 8 days and the washout of the 50 ppm addition of compound A, the butyrate concentration increased to 2 g/L. At this time another 100 ppm of compound A was added directly into the fermenter approximately 890 hours into the run. Upon addition of compound A the ethanol concentration began to immediately increase. After about 24 hours, the butyrate concentration began to decrease again declining almost 50% over the next 4 days. (See FIG. 3)

The results of Examples 5-8 show that in a 2-L butyrogenic reactor compound A had an inhibitory and bactericidal effect on the butyrogen population shortly after addition. In all three trials, addition of compound A showed a decrease in the first 24 hours in both OD and butyrate production with an increase in C2 production. The addition of the butyrogen retardant was shown to have beneficial effects at concentrations as low as 50 ppm.

Example 9

Fermenter operation was continued under the same operating conditions following the 100 ppm addition of compound A. After allowing 20 days for the complete wash out of compound A, 100 ppm of compound D was added directly into the fermenter approximately 1370 hours into the fermenter run. Upon the addition of compound D there was a sharp rise in the ethanol concentration and acetic acid concentration accompanied by a decrease in the butyrate production. The butanol concentration rose temporarily following the 100 ppm addition of compound D which again is believed to show a rapid conversion of the butyric acid to butanol as was seen in Example 5.

Example 10

For 12 days after the first injection of compound D into the fermenter, the fermenter was allowed to wash out compound D. Then 500 ppm of compound D was injected directly into the fermenter after about 1660 hours of fermenter operation. (See FIG. 3) The resulting concentrations of the $C_2$ and $C_4$ alcohols and acids from the time of adding the 500 ppm of compound D are shown in Table 10.

TABLE 10

| Addition Hr | OD @600 nm | EtOH g/L | Acetic acid g/L | n-Butanol g/L | Butyric acid g/L |
|---|---|---|---|---|---|
| 0 | 1.40 | 0.55 | 8.72 | 0.21 | 1.51 |
| 30 | 1.35 | 0.61 | 8.48 | 0.23 | 1.47 |
| 49 | 1.23 | 0.69 | 8.64 | 0.26 | 1.44 |
| 73 | 1.12 | 0.68 | 8.56 | 0.26 | 1.37 |
| 123 | 0.92 | 0.53 | 8.72 | 0.19 | 1.41 |
| 145 | 1.12 | 0.88 | 8.75 | 0.26 | 1.36 |
| 168 | 1.38 | 0.95 | 8.83 | 0.28 | 1.11 |
| 193 | 1.18 | 0.87 | 8.86 | 0.24 | 1.12 |
| 217 | 1.24 | 0.84 | 9.05 | 0.21 | 1.13 |
| 240 | 1.25 | 0.82 | 9.21 | 0.21 | 1.17 |

Figure 6:
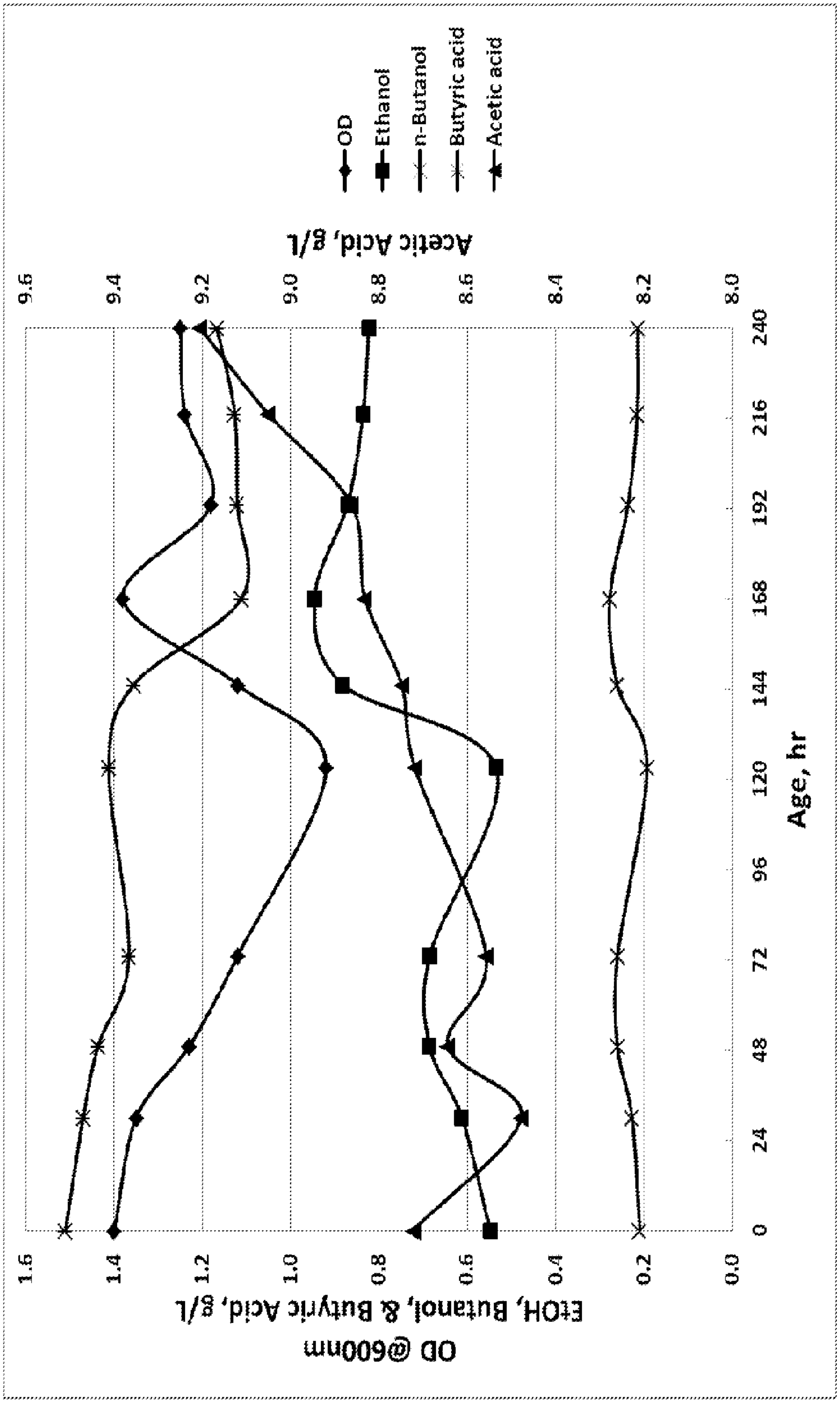
FIG. 6 is an expanded portion of the plot of FIG. 3 between approximately 1660 hours and 1900 hours.

The data and FIG. 6 show that immediately after addition of the compound D, the OD began to decrease showing reduction of cell growth. Furthermore, the concentrations of n-butyrate and n-butanol began to level off and slowly decrease whereas the concentrations of ethanol and acetate began to rise. Moreover, after the initial decrease, the OD began to rise with the concomitant increase of the $C_2$ compounds. This clearly established that the butyrogens were specifically inhibited whereas the homoacetogenic organisms were not inhibited and were able to grow and continue to produce the desirable $C_2$ products in the presence of compound D.

Example 11

Lehman, et al., in *An Acyl-Coenzyme A Dehydrogenase Assay Utilizing the Ferricenium Ion*, Analytical Biochemistry 186, pages 280-284 (1990), disclose an in vitro assay screening technique for acyl-CoA dehydrogenases for determining enzyme deficiencies in children. An adaptation of this technique was explored as a potential screening method for ascertaining potential butyrogen inhibitors.

An aqueous assay liquor is prepared such that each 1 milliliter sample contains 50 mM of TrisHCl buffer (pH 7.6); 0.05 mM of butyryl-CoA; 5 micromoles of FAD (flavin adenine dinucleotide) and 0.4 mM of ferrocenium. Whole cells of *C. tyrobutyricum* are lysed and are added to the assay liquor. Various compounds are added to the 1 milliliter samples at concentrations of 0.5 mM, 1.25 mM, 2.5 mM, 5.0 mM and 10 mM (a control sample containing no cell-free extract is also prepared). The abbreviation mM stands for millimolar.

To assure metabolic consistency among the samples a master batch of *C. tyrobutyricum* is prepared and harvested at the early log growth stage (approximate O.D. of between about 0.5 and 0.7). The master batch fermentation broth is centrifuged and rinsed with 50 mM TrisHCl buffer (pH 7.6), centrifuged and reconstituted with 50 mM TrisHCl buffer (pH 7.6) to be 10 times more concentrated than the original master batch. Aliquots of about 0.5 milliliter are placed into cryogenic vials (about 1.8 milliliter capacity) and frozen at −80° C. until needed. When needed, a vial is placed in an anoxic Coy chamber and allowed to thaw to room temperature. Once thawed, the cells are added to a 15 mL centrifuge tube and diluted with 0.5 mL of a 2 mg/mL solution of lysozyme (purchased from Aldrich) in 50 mM Tris-HCl (final concentration of lysozyme is about 1 mg/mL). The centrifuge tube is inverted 5 times, removed from the Coy chamber and allowed to incubate at 37° C. for 30 minutes. After incubation, the centrifuge tube is returned to the Coy Chamber and 50 μL of a 5% (v/v) solution of Triton-X 100 in 50 mM Tris-HCl buffer is added to the lysed cells. The centrifuge tube is vortexed in the Coy chamber for about 30 seconds, removed from the chamber and centrifuged for 15 minutes at 4000 rpm and 4° C. The tube is returned to the chamber and the cell-free extract (supernatant) is used to prepare the above described samples.

The samples are analyzed at various times by absorbance spectroscopy at 300 nm using a Thermo Scientific Evolution 300 UV/Vis spectrophotometer with a 7-cuvette carousel and Starna quartz cuvettes with a septum cap to determine the amount of reduction of ferrocenium. The sample is at laboratory temperature and is maintained under anaerobic conditions. Typically, the absorbance is measured over a period of about 10 to 20 minutes which is sufficient time for the absorbance to stop changing. A linear slope of the rate of change in absorbance during the period that the absorbance is changing is determined using Microsoft Excel® 2010 linear regression to generate a straight line from the data points. The more gradual the slope, the better inhibition because the enzyme is slower at reducing the ferrocenium in the assay sample. A dose-response curve is then determined for each compound by plotting the linear slope against the respective compound concentration. A linear slope is then determined for each compound using Microsoft Excel® 2010 linear regression to generate a straight line from the data points. The steeper the dose-response slope, the better the inhibition because the increased concentration of the compound causes more of a difference in enzyme activity. The dose-response slope generally has a broad standard of deviation due to experimental imprecision and slope determinations.

Compound A from Table 1 has a dose-response slope of about 8 which confirms that this technique has viability for in vitro screening. Table 11 provides the dose-response slope determinations for a variety of compounds.

TABLE 11

Dose-Response Slope for Various Compounds

| Compound | Dose-Response Slope |
|---|---|
| Ethyl 3-amino-4,4,4-trifluorocrotonate | 25 |
| 3-Trifluoromethyl-4-methoxybenzamide | 12 |
| Ethyl 3-trifluormethylbenzoate | 9 |
| Ethyl 4,4,4-trifluoro-3-(trifluoromethyl)crotonate | 8 |
| 4,4,4-Trifluorocrotonamide | 8 |
| Ethyl 2-(trifluoromethyl)benzoate | 8 |
| 3-(Trifluoromethyl)benzoate | 6 |
| Ethyl 4,4,4-trifluorocrotonate | 6 |
| t-Butyl crotonate (comparative) | 6 |
| 3-Trifluoromethyl-4-fluorobenzamide | 5 |
| Ethyl 4,4,4-trifluoro-2-methylcrotonate (comparative) | 2 |

Examples 12 to 15

Examples 12 through 15 are in vivo examples and standard media are used in each example as described in Tables 12 and 13(a), (b) and (c).

TABLE 12

Fermentation Medium Compositions

| Components | Amount per liter |
|---|---|
| Mineral solution, See Table 13(a) | 25 ml |
| Trace metal solution, See Table 13(b) | 2.5 ml |
| Vitamins solution, See Table 13(c) | 334 μl |
| Yeast Extract | 0.5 g |
| Adjust pH to 5.8 with NaOH | |
| Cysteine•HCl•$H_2O$ | 0.211 g |
| 2-(N-morpholino)ethanesulfonic acid | 20 g |

TABLE 13(a)

| Mineral Solution | |
|---|---|
| Components | Concentration (g/L) |
| NaCl | 0 |
| $NH_4Cl$ | 100 |
| KCl | 10 |
| $KH_2PO_4$ | 20 |
| $MgSO_4$•$7H_2O$ | 5 |
| $CaCl_2$•$2H_2O$ | 2 |

TABLE 13(b)

| Trace Metals Solution | |
|---|---|
| Components | Concentration (g/L) |
| Adjust the pH to 2.0 with HCl | |
| $MnSO_4$•$H_2O$ | 1.509 |
| $FeSO_4$•$7H_2O$ | 14.628 |
| $CoCl_2$•$6H_2O$ | 1.434 |
| $ZnSO_4$•$7H_2O$ | 0.784 |
| $NiCl_2$•$6H_2O$ | 0.311 |
| $Na_2SeO_4$ | 0.4 |
| $Na_2WO_4$•$2H_2O$ | 0.237 |
| Adjust the pH to 2.0 with HCl | |

TABLE 13(c)

| Vitamin Solution | |
|---|---|
| Components | Concentration (mg/L) |
| Pyridoxine•HCl | 0 |
| Thiamine•HCl | 300 |
| Roboflavin | 0 |
| Calcium Pantothenate | 300 |
| Thioctic acid | 0 |
| p-Aminobenzoic acid | 0 |
| Nicotinic acid | 15 |
| Vitamin B12 | 0 |
| Mercaptoethanesulfonic acid | 0 |
| Biotin | 150 |
| Folic acid | 0 |

Example 12

Ethyl 4,4,4-trifluoro-3-aminocrotonate is evaluated in a series of batch fermentations to determine the growth response of butyrogens to the presence of this compound at varying concentrations. The batch fermentations are conducted by anoxically filling 100 mL serum bottles with 20 mL of media having the composition given in Tables 12 and 13. About 0.2 mL of a 50% w/w solution of fructose in water (final fructose concentration about 5 g/L) is provided in the bottles.

Each bottle is inoculated with 2 mL of seed culture inoculum of the strict butyrogen *Clostridium tyrobutyricum*, which has an OD of about 0.90 (which upon a 10 times dilution provides a starting OD for the fermentation of about 0.09). The bottles are maintained at a temperature of 37° C. Twenty five hours after inoculation of the bottles with the bacteria, the fermentation media have optical densities ranging from 0.70-0.85. At this time the compound is added to different bottles as a solution in 100 μL media in the amounts indicated in Table 14. The bacteria are in mid-log phase growth at the time of the inoculation. The fermentation process is allowed to progress at 37° C. At selected intervals of time, bacterial growth is measured by reading the optical density (OD) of the fermentation liquid. Optical density is measured by anoxically removing an aliquot of fermentation liquid and adding it to a disposable cuvette. OD's ranging between 0.01 and 0.4 are measured directly, while OD's greater than 0.4 are measure after performing a 1/10 dilution with water.

TABLE 14

| O.D. Response to Varying Inhibitor Concentrations | | | | | |
|---|---|---|---|---|---|
| Hours | Control | 100 ppm | 250 ppm | 500 ppm | 1000 ppm |
| 22.5 | 0.76 | 0.84 | 0.86 | 0.80 | 0.70 |
| 28.5 | 1.82 | 1.48 | 1.87 | 0.93 | 0.77 |
| 43.5 | 1.67 | 1.53 | 1.92 | 1.00 | 0.78 |

As can be seen from the data in Table 14, the control had the greatest increase in O.D. between 22.5 and 28.5 hours thus indicating that this crotonate-like compound had an inhibitory effect on the butyrogen.

Example 13

Ethyl 3-(trifluoromethyl)benzoate is evaluated in a series of batch fermentations to determine the growth response of butyrogens to the presence of this compound at varying concentrations. The batch fermentations are conducted by anoxically filling 100 mL serum bottles with 15 mL of media having the composition given in Tables 12 and 13. About 0.15 mL of a 50% w/w solution of fructose in water (final fructose concentration about 5 g/L) is provided in the bottles. Duplicate runs are conducted for each concentration.

Each bottle is inoculated with 1.5 mL of seed culture inoculum of the strict butyrogen *Clostridium tyrobutyricum*, which has an OD of about 0.40 (which upon a 10 times dilution provides a starting OD for the fermentation of about 0.04). The bottles are maintained at a temperature of 37° C. Two hours after inoculation of the bottles with the bacteria, the compound is added to different bottles as a solution in 50 μL of N-methylpyrrolidone in the amounts indicated in Table 15. The fermentation process is allowed to progress at 37° C. At selected intervals of time, bacterial growth is measured by reading the optical density (OD) of the fermentation liquid. Optical density is measured by anoxically removing an aliquot of fermentation liquid and adding it to a disposable cuvette. OD's ranging between 0.01 and 0.4 are measured directly, while OD's greater than 0.4 are measure after performing a 1/10 dilution with water.

TABLE 15

| O.D. Response to Varying Inhibitor Concentrations | | | | | | |
|---|---|---|---|---|---|---|
| Hours | Control A | Control B | 500 ppm A | 500 ppm B | 1000 ppm A | 1000 ppm B |
| 0 | 0.04 | 0.04 | 0.04 | 0.04 | 0.04 | 0.04 |
| 2 | 0.08 | 0.08 | 0.09 | 0.09 | 0.09 | 0.09 |
| 3.5 | 0.14 | 0.14 | 0.14 | 0.14 | 0.15 | 0.15 |
| 5.25 | 0.37 | 0.37 | 0.21 | 0.23 | 0.21 | 0.22 |
| 11 | 1.73 | 1.65 | 0.90 | 0.89 | 0.90 | 0.87 |
| 20.5 | 1.80 | 1.76 | 1.53 | 1.44 | 1.42 | 1.37 |

The concentration of butyric acid is determined by gas chromatography for several of the above samples at the stated points in time. The butyrate production is calculated based upon peak area calculations generated by the gas chromatograph. At 11 hours, the concentration of butyric acid for each of the controls is about 0.95 gram per liter, and the concentration of butyric acid for the samples containing 500 ppm of the inhibitor are about 0.6 gram per liter.

Example 14

In this example ethyl 4,4,4-trifluoro-3-(trifluoromethyl) crotonate and ethyl 3-trifluoromethyl-4-methoxybenzoate are evaluated by batch fermentation. The batch fermentations are conducted by anoxically filling 100 mL serum bottles with 15 mL of media having the composition given in Tables 12 and 13. About 0.15 mL of a 50% w/w solution of fructose in water (final fructose concentration about 5 g/L) is provided in the bottles. Duplicate runs are conducted for each concentration.

Each bottle is inoculated with 1.5 mL of seed culture inoculum of the strict butyrogen *Clostridium tyrobutyricum*, which has an OD of about 0.42 (which upon a 10 times dilution provides a starting OD for the fermentation of about 0.042). The bottles are maintained at a temperature of 37° C. Two hours after inoculation of the bottles with the bacteria, the compound is added to different bottles as a solution in 50 μL of N-methylpyrrolidone in the amounts indicated in Table 16 and 17. The fermentation process is allowed to progress at 37° C. At selected intervals of time, bacterial growth is measured by reading the optical density (OD) of the fermentation liquid. Optical density is measured by anoxically removing an aliquot of fermentation liquid and adding it to a disposable cuvette. OD's ranging between 0.01 and 0.4 are measured directly, while OD's greater than 0.4 are measured after performing a 1/10 dilution with water. The results of control A and control B runs are repeated in each Table.

TABLE 16

O.D. Response to Ethyl 4,4,4-trifluoro-3-(trifluoromethyl)crotonate

| Hours | Control A | Control B | 5 mM A | 5 mM B |
|---|---|---|---|---|
| 0 | 0.42 | 0.42 | 0.42 | 0.42 |
| 2 | 0.11 | 0.11 | 0.10 | 0.10 |
| 4.5 | 0.28 | 0.27 | 0.14 | 0.11 |
| 6 | 0.41 | 0.13 | 0.13 | 0.13 |
| 24 | 1.66 | 1.63 | 0.12 | 0.12 |

TABLE 17

O.D. Response to Ethyl 3-trifluoromethyl-4-methoxybenzoate

| Hours | Control A | Control B | 5 mM A | 5 mM B | 10 mM A | 10 mM B |
|---|---|---|---|---|---|---|
| 0 | 0.42 | 0.42 | 0.42 | 0.42 | 0.42 | 0.42 |
| 2 | 0.11 | 0.11 | 0.11 | 0.12 | 0.11 | 0.11 |
| 4.5 | 0.28 | 0.27 | 0.20 | 0.18 | 0.24 | 0.23 |
| 6 | 0.41 | 0.13 | 0.16 | 0.10 | 0.12 | 0.13 |
| 24 | 1.66 | 1.63 | 1.23 | 0.91 | 1.22 | 1.19 |

The concentration of butyric acid is determined by gas chromatography using the procedure set forth in Example 13. Tables 18 and 19 summarize the results with the production being reported in grams per liter. The control is reported only in Table 18.

TABLE 18

Butyrate Production Using Ethyl 4,4,4-trifluoro-3-(trifluoromethyl)crotonate

| Hours | Control A | Control B | 5 mM A | 5 mM B |
|---|---|---|---|---|
| 2 | 0 | 0.02 | 0.03 | 0 |
| 4.5 | 0.10 | 0.09 | 0.04 | 0.04 |
| 6 | 0.21 | 0.26 | 0.06 | 0.05 |
| 24 | 1.11 | 1.12 | 0.10 | 0.08 |

TABLE 19

Butyrate Production Using Ethyl 3-trifluoromethyl-4-methoxybenzoate

| Hours | 5 mM A | 5 mM B | 10 mM A | 10 mM B |
|---|---|---|---|---|
| 2 | 0.04 | 0 | 0.03 | 0.03 |
| 4.5 | 0.15 | 0.67 | 0.69 | 0.67 |
| 6 | 0.19 | 0.10 | 0.11 | 0.10 |
| 24 | 1.15 | 0.14 | 0.19 | 0.17 |

Example 15

In this example various crotonate-like compounds on are evaluated for toxicity to *C. autoethanogenum* by batch fermentation using syngas substrate. The batch fermentations are conducted by anoxically filling 100 mL serum bottles with 10 mL of media having the composition given in Tables 12 and 13. Duplicate runs are conducted for each concentration. The compounds are:

C-1 Ethyl 4,4,4-trifluoro-3-(trifluoromethyl)crotonate

C-4 4,4,4-Trifluorocrotonamide

C-9 Ethyl 4,4,4-Trifluoro-3-(amino)crotonate

C-18 3 trifluoromethyl-4-methoxybenzoate.

Each bottle is inoculated with 1.0 mL of seed culture inoculum from an active fermenter using syngas substrate and containing *Clostridium autoethanogenum*, which inoculum has an OD of about 4.92 (which upon a 10 times dilution provides a starting OD for the fermentation of about 0.49). The bottles are gased with syngas to about 100 kilopascals and maintained at a temperature of 37° C. The bottles are regassed with syngas every 8 to 12 hours. The syngas has the approximate composition set forth in Examples 6 to 10. Twenty four hours after inoculation of the bottles with the bacteria, the compounds are added to different bottles as a solution in 50 μL of N-methylpyrrolidone in the amounts indicated in Tables 20 and 21. The fermentation process is allowed to progress at 37° C. At selected intervals of time, bacterial growth is measured by reading the OD of the fermentation liquid using a Thermo Spectronic Genesys 20 spectrophotometer. Optical density is measured by anoxically removing an aliquot of fermentation liquid and adding it to a disposable cuvette. OD's ranging between 0.01 and 0.4 are measured using fermentation liquid directly, while OD's greater than 0.4 are measure after performing a 1/10 dilution with water.

TABLE 20

O.D. Response to Various Inhibitors

| Hours | Control | C-1 A | C-1 B | C-4 A | C-4 B | C-9 A | C-9 B | C-18 A | C-19 B |
|---|---|---|---|---|---|---|---|---|---|
| 0 | 0.49 | 0.49 | 0.49 | 0.49 | 0.49 | 0.49 | 0.49 | 0.49 | 0.49 |
| 2.5 | 0.49 | 0.42 | 0.46 | 0.40 | 0.42 | 0.40 | 0.42 | 0.47 | 0.41 |
| 6.5 | 0.41 | 0.42 | 0.46 | 0.4 | 0.43 | 0.42 | 0.46 | 0.44 | 0.44 |

TABLE 20-continued

| O.D. Response to Various Inhibitors | | | | | | | | | |
|---|---|---|---|---|---|---|---|---|---|
| Hours | Control | C-1 A | C-1 B | C-4 A | C-4 B | C-9 A | C-9 B | C-18 A | C-19 B |
| 24.5 | 1.29 | 1.17 | 1.08 | 1.03 | 1.09 | 1.14 | 0.97 | 1.15 | 1.18 |
| 30.5 | 1.36 | 1.15 | 1.22 | 1.31 | 1.33 | 1.28 | 1.47 | 1.32 | 1.28 |
| 47.5 | 1.86 | 0.66 | 0.67 | 1.7 | 1.64 | 1.67 | 2.12 | 1.73 | 1.75 |

The concentration of butyric acid is determined by gas chromatography using the procedure set forth in Example 13. Table 21 summarize the results with the production being reported in grams per liter.

TABLE 21

| O.D. Response of Various Inhibitors on *C. autoethanogenum* | | | | | |
|---|---|---|---|---|---|
| Hours | Control | C-1 | C-4 | C-9 | C-18 |
| 0 | 0.49 | 0.49 | 0.49 | 0.49 | 0.49 |
| 2.5 | 0.49 | 0.44 | 0.41 | 0.41 | 0.44 |
| 6.5 | 0.41 | 0.44 | 0.42 | 0.44 | 0.44 |
| 24.5 | 1.29 | 1.12 | 1.06 | 1.06 | 1.16 |
| 30.5 | 1.36 | 1.18 | 1.32 | 1.38 | 1.30 |
| 47.5 | 1.86 | 0.66 | 1.67 | 1.90 | 1.74 |
| 56 | 1.91 | 0.58 | 1.72 | 1.98 | 1.88 |

It is claimed:

1. A process for the metabolic conversion of substrate to light oxygenates comprising:

a. contacting in a fermentation liquid containing said substrate with microorganisms capable of bioconverting the substrate to light oxygenates under fermentation conditions, said fermentation liquid being susceptible to a presence of contaminating bacteria capable of producing at least one of butyrate or butanol from said substrate or from said light oxygenates through a butyryl CoA enzyme; and b. providing in said fermentation liquid a sufficient amount of a crotonate-like compound to restrict the production of said at least one of butyrate or butanol by a butyryl-CoA dehydrogenase, wherein the crotonate-like compound is represented by the structural formula:

$R^2(R^3)C{=}C(H)C(O)R^1$ I.

or $R^2\text{-}A\text{-}C(O)R^1$ II.

wherein:

$R^1$ is —OH, —$OR^5$, or —$N(R^4)_2$, wherein $R^5$ is hydrocarbyl and each $R^4$ may be the same or different and is hydrogen or hydrocarbyl;

$R^2$ is hydrogen, —$NH_2$, —OH or —$CX_3$ wherein each X may be the same or different and is hydrogen or halogen;

$R^3$ is hydrocarbyl of 1 to 18 carbons which may be unsubstituted or substituted with —OH, alkoxyl of 1 to about 6 carbons, or halogen;

A is an aromatic moiety having 5 or 6 ring atoms which may be all carbon atoms or may be heterocyclic with one hetero atom selected from the group consisting of oxygen and nitrogen which aromatic moiety has —$R^2$ at the 2 position wherein —$R^2$ is as defined above and which aromatic moiety may be unsubstituted or substituted at one or more of the higher carbon positions with (i) hydrocarbyl of 1 to 18 carbons which may be substituted with —OH, alkoxyl of 1 to about 6 carbons, or halogen, (ii) —$OR^6$ wherein $R^6$ is lower alkyl, (iii) —$N(R^7)_2$ wherein each $R^7$ is the same or different and is hydrogen or hydrocarbyl or (iv) halogen;

with the proviso that in structural formula I, at least one of $R^2$ and $R^3$ is or is substituted with haloalkyl and that in formula II at least the 2 or 3 carbon position of the aryl moiety is substituted with an electron withdrawing group selected from the group consisting of halogen and haloalkyl.

2. A method of restricting the production of butyrate and/or butanol in an anaerobic fermentation of a gas substrate comprising at least one of CO and a mixture of $CO_2$ with hydrogen, the method comprising:

a. passing the gas stream to an anaerobic fermentation zone containing at least one species of anaerobic microorganism capable of producing an liquid product comprising light oxygenates;

b. converting at least a portion of the gas stream to the liquid product by contact of the microorganism in the fermentation zone with the gas stream;

c. providing at least one crotonate-like compound in the fermentation liquid in an amount effective to restrict production of butyrate and/or butanol by butyryl-CoA dehydrogenase, said crotonate-like compound represented by the structural formula $R^2(R^3)C{=}C(H)C(O)R^1$ I.

or $R^2\text{-}A\text{-}C(O)R^1$ II.

wherein:

$R^1$ is —OH, —$OR^5$, or —$N(R^4)_2$, wherein $R^5$ is hydrocarbyl and each $R^4$ may be the same or different and is hydrogen or hydrocarbyl;

$R^2$ is hydrogen, —$NH_2$, —OH or —$CX_3$ wherein each X may be the same or different and is hydrogen or halogen;

$R^3$ is hydrocarbyl of 1 to 18 carbons which may be unsubstituted or substituted with —OH, alkoxyl of 1 to about 6 carbons, or halogen;

A is an aromatic moiety having 5 or 6 ring atoms which may be all carbon atoms or may be heterocyclic with one hetero atom selected from the group consisting of oxygen and nitrogen which aromatic moiety has —$R^2$ at the 2 position wherein —$R^2$ is as defined above and which may be unsubstituted or substituted at one or more of the higher carbon positions with (i) hydrocarbyl of 1 to 18 carbons which may be substituted with —OH, alkoxyl of 1 to about 6 carbons, or halogen, (ii) —$OR^6$ wherein $R^6$ is lower alkyl, (iii) —$N(R^7)_2$ wherein each $R^7$ is the same or different and is hydrogen or hydrocarbyl or (iv) halogen;

with the proviso that in structural formula I, at least one of $R^2$ and $R^3$ is or is substituted with haloalkyl and that in formula II at least the 2 or 3 carbon position of the aryl moiety is substituted with an electron withdrawing group selected from the group consisting of halogen and haloalkyl;

d. withdrawing fermentation liquid containing the liquid product from the fermentation zone; and e. recovering the liquid product from the fermentation liquid.

3. The method of claim 2 wherein the fermentation zone contains at least one of a homoacetogenic or heteroacetogenic microorganism for the production of a liquid product comprising ethanol or acetate and is contaminated with a butyrogenic microorganism that produces at least one of butyrate or butanol.

4. The method of claim 3 wherein the fermentation zone contains a homoacetogenic microorganism that comprises at least one of *Clostridium autoethanogenum, Clostridium ljungdahlii, Clostridium ragsdalei*, and *Clostridium coskatii* and the fermentation zone produces a liquid product comprising at least one of acetate and ethanol.

5. The method of claim 2 wherein the fermentation zone comprises a suspended cell bioreactor that suspends the anaerobic microorganism in the fermentation liquid and the at least one crotonate-like compound enters the bioreactor with a media mixture that flows into the fermentation liquid.

6. The method of claim 2 wherein the fermentation zone comprises a membrane supported bioreactor.

7. The method of claim 2 wherein the crotonate-like compound is represented by the formula:

$$R^2(R^3)C{=}C(H)C(O)R^1 \quad \text{III.}$$

or $$R^2\text{-A-}C(O)R^1 \quad \text{IV.}$$

wherein:

in formula III, $R^2$ is —OH, —$NH_2$ or —$CX_3$ wherein X is halogen and $R^3$ is —$CX_3$ wherein X is halogen, and in formula IV, the aryl is phenyl and at least one of the 2 and 3 position carbons of the phenyl moiety is —$CX_3$ wherein X is halogen.

8. The method of claim 7 wherein the at least one crotonate-like compound comprises at least one of alkyl 4,4,4-trifluoro-3-(trifluoromethyl)crotonate; 4,4,4-trifluoro-3-(trifluoromethyl)crotonic acid; 4,4,4-trifluoro-3-(trifluoromethyl) crotonamide; 2-trifluoromethylbenzoic acid; 2-trifluoromethylbenzamide; alkyl 2-trifluoromethylbenzoate; 3-trifluoromethylbenzoic acid; 3-trifluoromethylbenzamide; alkyl 3-trifluoromethylbenzoate; 2-amino-3-trifluoromethylbenzoic acid; 2-amino-3-trifluoromethylbenzamide; alkyl 2-amino-3-trifluoromethylbenzoate; 3-trifluoro-4-methoxybenzoic acid; 3-trifluoro-4-methoxybenzamide; alkyl 3-trifluoro-4-methoxybenzoate; 3-trifluoromethyl-4-fluorobenzoic acid; 3-trifluoromethyl-4-fluorobenzamide; alkyl 3-trifluoromethyl-4-fluorobenzoate; 3-trifluoromethyl-5-trifluoromethylbenzoic acid; 3-trifluoromethyl-5-trifluoromethylbenzamide; alkyl 3-trifluoromethyl-5-trifluoromethylbenzoate; 3-amino substituted crotonates such as 4,4,4-trifluoro-3-aminocrotonic acid; 4,4,4-trifluoro-3-aminocrotonamide; and alkyl 4,4,4-trifluoro-3-aminocrotonate wherein the alkyl is 1 to 4 carbons.

9. The method of claim 2 wherein the anaerobic microorganism comprises a heteroacetogen that produces liquid products having at least 2 to 3 carbon atoms and the liquid product comprises at least one of acetic acid, ethanol, propanol, and propionic acid.

10. The method of claim 2 wherein the at least one crotonate-like compound is added in an amount sufficient to produce a concentration of at least 10 ppm by mass in the fermentation liquid.

11. The method of claim 2 wherein the at least one crotonate-like compound is added to the fermentation zone as single dose in an amount of at least 50 ppm by mass.

12. The method of claim 2 wherein the fermentation zone comprises a membrane supported bioreactor and the at least one crotonate-like compound is added to the fermentation liquid.

13. The method of claim 2 wherein the fermentation zone contains more than one species of anaerobic microorganisms.

14. The method of claim 13 wherein the crotonate-like compound is represented by the formula:

$$R^2(R^3)C{=}C(H)C(O)R^1 \quad \text{III.}$$

or $$R^2\text{-A-}C(O)R^1 \quad \text{IV.}$$

wherein:

in formula III, $R^2$ is —OH, —$NH_2$ or —$CX_3$ wherein X is fluorine, and $R^3$ is —$CX_3$ wherein X is fluorine, and in formula IV, the aryl is phenyl and at least one of the 2 and 3 position carbons of the phenyl moiety is —$CX_3$ wherein X is fluorine.

15. The method of claim 13 wherein the fermentation zone contains a homoacetogenic microorganism for the production of a liquid product comprising ethanol and a butyrogenic microorganism that produces at least one of butyrate or butanol.

16. The method of claim 13 wherein the anaerobic microorganism comprises a heteroacetogen that produces liquid products having at least 2 to 3 carbon atoms and the liquid product comprises at least one of acetic acid, ethanol, propanol, and propionic acid.

17. The method of claim 13 wherein the at least one crotonate-like compound is added to the fermentation liquid at a concentration of at least 10 ppm.

18. A method of producing a product comprising a C2 oxygenate by the fermentation of a gas substrate comprising at least one of CO and a mixture of $CO_2$ with hydrogen using a homoacetogenic microorganism to convert the gas stream to the product, the method comprising:

a. passing the gas substrate stream to a fermentation zone containing an anaerobic microorganism and a fermentation liquid;

b. converting the gas substrate stream to the product by contact of the anaerobic microorganism in the fermentation zone with the gas substrate stream;

c. providing at least one crotonate-like compound to the fermentation liquid in an amount sufficient to inhibit a production of butyrate and/or butanol by butyryl-CoA dehydrogenase by at least one species of microorganism in the fermentation zone, said crotonate-like compound represented by the structural formula $$R^2(R^3)C{=}C(H)C(O)R^1 \quad \text{I.}$$

or $$R^2\text{-A-}C(O)R^1 \quad \text{II.}$$

wherein:

$R^1$ is —OH, —$OR^5$, or —$N(R^4)_2$, wherein $R^5$ is hydrocarbyl and each $R^4$ may be the same or different and is hydrogen or hydrocarbyl;

$R^2$ is hydrogen, —$NH_2$, —OH or —$CX_3$ wherein each X may be the same or different and is hydrogen or halogen;

$R^3$ is hydrocarbyl of 1 to 18 carbons which may be unsubstituted or substituted with —OH, alkoxyl of 1 to about 6 carbons, or halogen;

A is an aromatic moiety having 5 or 6 ring atoms which may be all carbon atoms or may be heterocyclic with one hetero atom selected from the group consisting of oxygen and nitrogen which aromatic moiety has —$R^2$ at the 2 position wherein —$R^2$ is as defined above and which aromatic moiety may be unsubstituted or substituted at one or more of the higher carbon positions with (i) hydrocarbyl of 1 to 18 carbons which may be substituted with —OH, alkoxyl of 1 to about 6 carbons, or halogen, (ii) —$OR^6$ wherein $R^6$ is lower alkyl, (iii) —$N(R^7)_2$ wherein each $R^7$ is the same or different and is hydrogen or hydrocarbyl or (iv) halogen;

with the proviso that in structural formula I, at least one of $R^2$ and $R^3$ is or is substituted with haloalkyl and that in formula II at least the 2 or 3 carbon position of the aryl moiety is substituted with an electron withdrawing group selected from the group consisting of halogen and haloalkyl;

d. withdrawing the product containing fermentation liquid from the fermentation zone; and e. recovering the product from the fermentation liquid.

19. The method of claim 18 wherein the crotonate-like compound is represented by the formula:

$$R^2(R^3)C{=}C(H)C(O)R^1 \qquad III.$$

or $$R^2\text{-A-}C(O)R^1 \qquad IV.$$

wherein:

in formula III, $R^2$ is —OH, —$NH_2$ or —$CX_3$ wherein X is fluorine, and $R^3$ is —$CX_3$ wherein X is fluorine, and in formula IV, the aryl is phenyl and at least one of the 2 and 3 position carbons of the phenyl moiety is —$CX_3$ wherein X is fluorine.

* * * * *